(12) United States Patent
Curtiss, III et al.

(10) Patent No.: US 6,610,529 B1
(45) Date of Patent: *Aug. 26, 2003

(54) RECOMBINANT BACTERIAL SYSTEM WITH ENVIRONMENTALLY LIMITED VIABILITY

(75) Inventors: Roy Curtiss, III, St. Louis, MO (US); Steven A. Tinge, Belleville, IL (US)

(73) Assignee: Washington University, Saint Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/761,769

(22) Filed: Dec. 6, 1996

Related U.S. Application Data

(63) Continuation-in-part of application No. 08/473,789, filed on Jun. 7, 1995, now abandoned.

(51) Int. Cl.[7] .......................... C12N 1/21; A01N 63/00; A61K 39/108; C12P 12/06

(52) U.S. Cl. .................. 435/252.3; 435/69.1; 435/442; 435/471; 435/481; 424/93.1; 424/93.2; 424/93.48; 424/257.11; 424/258.11; 935/22; 935/23; 935/33; 935/43

(58) Field of Search .................. 424/93.1, 93.2, 424/93.48, 257.1, 258.1, 200; 435/69.1, 172.1, 172.2, 172.3, 320.1, 252.3; 935/22, 23, 33, 43

(56) References Cited

U.S. PATENT DOCUMENTS 5,681,745 A * 10/1997 Szagranski et al. ......... 435/325
5,702,916 A * 12/1997 Molin et al. ................ 435/69.1

OTHER PUBLICATIONS

Curtiss, III. "The Release of Genetically–engineered Microorganisms". Proceedings of the First International Conference on the Release of Genetically–engineered microorganisms. (Sussman et al. editors., Academic Press, pp. 7–19, 1988.*
Cardenas et al. Clinical Microbiology Reviews 5(3): 328–342, 1992.*
Sigwart et al. Injection and Immunity 57 (6) : 1858–1861, 1989.*
Gerdes et al. Proc. Natl. Acad. Sci 83: 3116–3120, 1986.*
Ramos et al. Bio/Technology 13: 35–37, 1995.*
Galan et al. Gene 94 : 29–35, 1990.*
Guzman et al. Journal of Bacteriology 177 (14): 4121–4130, 1995.*

* cited by examiner

Primary Examiner—Lynette R. F. Smith
Assistant Examiner—Robert A. Zeman
(74) Attorney, Agent, or Firm—Thompson Coburn LLP

(57) ABSTRACT

Disclosed is an Environmentally Limited Viability System (ELVS) for microorganisms based on differences between permissive and non-permissive environments. Viability of the microorganisms are limited to a permissive environment by specifically expressing one or more essential genes only in the permissive environment, and/or expressing one or more lethal genes only in the non-permissive environment. Temporary viability in a non-permissive environment can be achieved by temporarily expressing one or more essential genes in a non-permissive environment, and/or temporarily delaying expression of one or more lethal genes in the non-permissive environment. Environmentally Limited Viability Systems are also disclosed involving coordinate expression of a combination of essential genes and lethal genes. Microorganisms containing an Environmentally Limited Viability System are useful for release into permissive and non-permissive environments. Temperature regulated Environmentally Limited Viability Systems and delayed death Environmentally Limited Viability Systems are particularly suited for delivery of expression products, such as antigens, using recombinant avirulent Salmonella by limiting their growth to the warmer environment inside the host, or by allowing growth for only a limited time in the host.

16 Claims, 14 Drawing Sheets

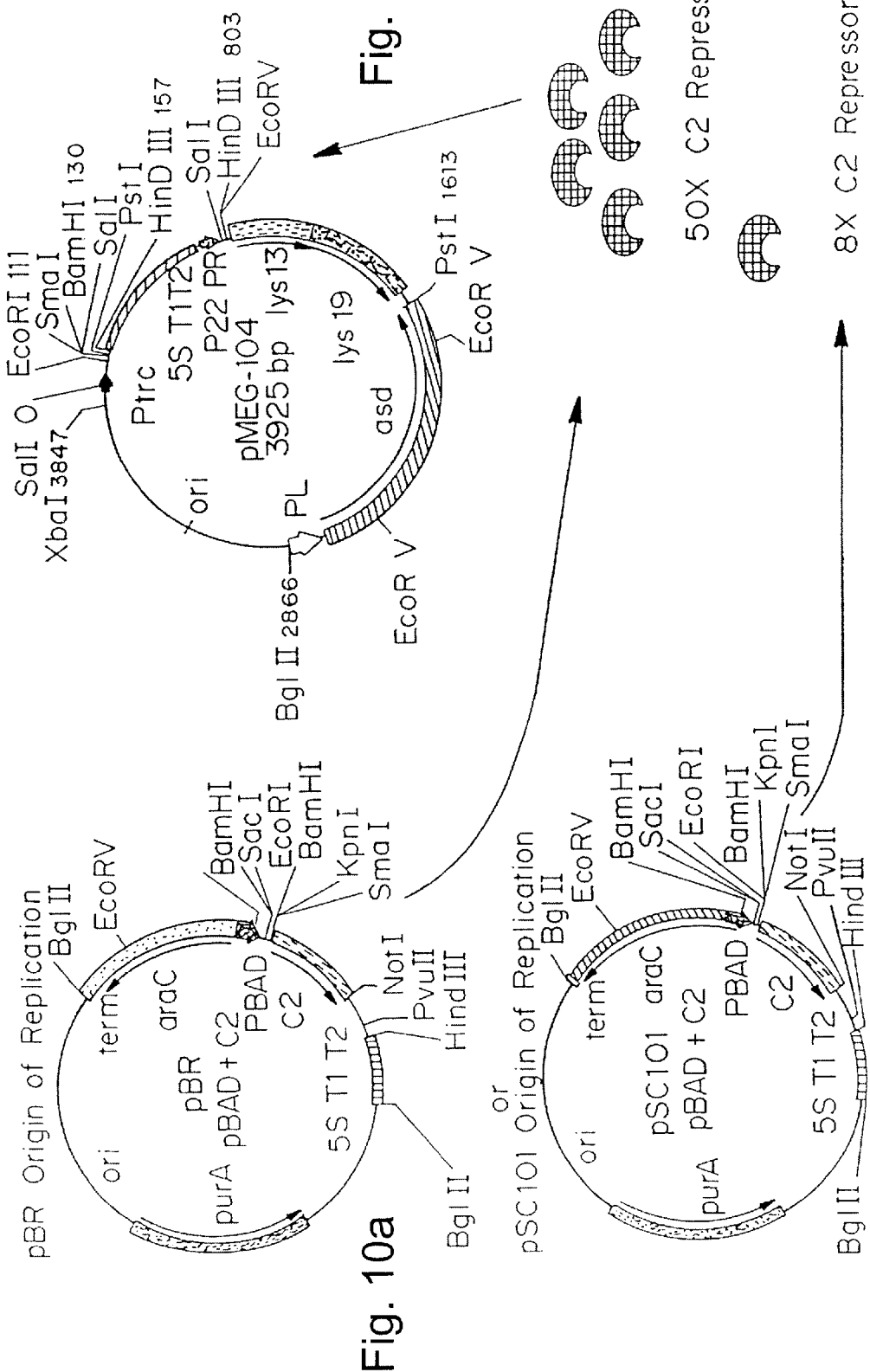

RECOMBINANT BACTERIAL SYSTEM WITH ENVIRONMENTALLY LIMITED VIABILITY

CROSS-REFERENCE TO RELATED APPLICATIONS

This application is a continuation-in-part of U.S. application Ser. No. 08/473,789 filed Jun. 7, 1995 now abandoned.

STATEMENT REGARDING FEDERALLY SPONSORED RESEARCH

The United States Government has rights to this invention pursuant to PHS Grants DE06669, A124533, and HD29099.

BACKGROUND OF THE INVENTION

The invention relates to recombinant microorganisms with environmentally limited growth and viability, and more particularly to recombinant microorganisms that may only survive in a host organism for a defined period of time and will not grow outside of the host organism.

Genetically engineered microorganisms have widespread utility and importance. For example, they can be used to produce foreign proteins, and thus can be used industrially for synthesis of products such as interferons, insulin, and growth hormone; they can also be used as antigen delivery systems to produce an immune response. However, it is undesirable for the genetically-engineered microorganism to persist in the environment.

Physical containment was the first means used to control the spread of genetically engineered microorganisms. More sophisticated means were then developed where microorganisms were contained by introducing debilitative mutations that prevent their growth in the absence of specific growth conditions, such as a particular amino acid. U.S. Pat. No. 4,190,495 discloses microorganisms with multiple mutations to prevent growth or genetic transfer outside of the controlled laboratory conditions.

Suicide plasmids have been described for use in biological containment of microorganisms (Molin et al., *Annual Review of Microbiology* 47:139–166 (1993)). Suicide plasmids generally use differential expression of a specific gene in and out of a controlled environment to prevent survival of the microorganism outside of the controlled environment. The use of suicide plasmids or systems has been limited to the expression of a required gene, or the repression of a lethal gene, under laboratory or other artificial conditions. In the absence of the supplied stimulus, the lethal gene becomes expressed. Either event leads to cell death either directly or due to a severe competitive disadvantage. Most suicide systems depend upon expression of a gene that is actively toxic to the microorganism. A common problem with active suicide systems is the high selective pressure for mutations in the killing gene. This is analyzed, for example, by Knudsen and Karlström, *Applied and Environmental Microbiology* 57(1):85–92 (1991), who used a suicide function controlled by $LacI^q$ binding to Plac to repress expression of relF, thus preventing the suicide that would be caused by synthesis of the relF gene product. Expression of RelF, and thus display of the suicide phenotype, required the addition of IPTG. This system therefore served as a laboratory model to study induction of host killing within the plasmid-containing host or after transfer of the plasmid to a host lacking the lacI encoded repressor. The efficacy of the system was limited on the one hand by mutations that made killing by the relF gene product ineffective, and on the other hand by low level expression of relF even in the absence of added IPTG such that cells in the culture grew slowly.

Molin et al., *Bio/Technology* 5:1315–1318 (1987), describes the use of hok, encoding a small peptide that is lethal when expressed in many bacterial species, to prevent survival of a recombinant microorganism when outside of a controlled fermenter environment. The hok gene is homologous to the relF gene. Molin et al. (1987) uses an invertible promoter to control expression of hok. Stochastic inversion of the inactive promoter to the active orientation causes the bacterial population to dwindle due to the death of a predetermined fraction of the cells per unit time. This stochastic cell death is dependent on the relative expression of the fimB and fimE genes which control the flip-flop orientation of the invertible promoter. This system does not lead to a rapid drop in bacterial population density except under ideal laboratory conditions.

Molin and Kjelleberg, *AMBIO* 22(4):242–245 (1993), and Ramos et al., *Bio/Technology* 13:35–37 (1995) have hypothesized that microorganisms for release in natural environments might be regulated by suicide genes. Molin and Kjelleberg describe the use of a suicide gene regulated by general or specific starvation. Ramos et al. disclose the use of gef family genes, of which hok and relF are members, and nuclease genes, as suicide genes. Ramos et al. also described killing by these gene products expressed upon IPTG induction of the inducible Plac fused to the gef gene. Ramos et al. describe regulation of the suicide function by loss of a specific nutrient or condition, such as occurs outside of artificially controlled conditions, and by linking the regulatory stimulus to the task of the microorganism. This was accomplished by controlling the rate of inversion of a promoter which in one orientation causes expression of relF, resulting in cell death. This system, of course, only leads to a gradual loss in the viability of the cell population once the cells are in an environment lacking a nutrient. Ramos et al. also suggests the use of biological containment to make live antigen delivery systems feasible. However, Ramos et al. (page 37) points out that the complexity of the human gut precludes the design of control circuits based on specific stimuli, suggesting containment based on differential growth rates in and out of the gut. Ramos et al. does not suggest any regulatory system that could achieve this goal.

Live bacterial vaccines have been described that express a desired antigen and colonize the intestinal tract of animals (Curtiss et al., *Curr. Topics Micro. Immun.* 146:35–49 (1989); Curtiss, *Attenuated Salmonella Strains as Live Vectors for the Expression of Foreign Antigens*, in *New Generation Vaccines* (Woodrow and Levine, eds., Marcel Dekker, New York, 1990) pages 161–188; Schödel, *Infection* 20(l):1–8 (1992); Cardenas and Clements, *Clinical Micro. Rev.* 5(3):328–342 (1992)). Most work to date has used avirulent *Salmonella typhimurium* strains synthesizing various foreign antigens for immunization of mice, chickens and pigs. Several avirulent *S. typhi* vectors have been evaluated in human volunteers (Tacket et al., *Infect. Immun.* 60:536–541 (1992)) and several phase I clinical trials with recombinant avirulent *S. typhi.* strains are in progress in the U.S. and Europe.

Although research progress toward expanding and further improving the recombinant avirulent Salmonella antigen delivery strategy has progressed at a reasonable rate, commercial development of recombinant vaccines for the control of infectious diseases of animals or humans has been slow. An important safety advantage of the live attenuated bacterial vaccine vectors as compared to the use of viral vector based vaccines is the ability to treat an immunized patient with oral ciprofloxacin or amoxicillin, should an adverse reaction occur. However, current live bacterial vaccines have the disadvantage that oral administration leads to fecal shedding, with the potential risk that the bacterial vaccine strain will proliferate in nature and infect individuals not selected for immunization. It is known, for example, that fecal coliforms can persist for extended periods under field conditions, with only moderate reductions in numbers (Temple et al., *Appl. Environ. Microbiol.* 40:794–797 (1980)). There is also concern that these surviving vaccine strains will transmit their cloned genetic information to more robust microorganisms encountered in nature with not always predictable consequences. Although the transmission of most expressed genes to wild-type microbial species would not be harmful, some recombinant vectors expressing genes for sperm-specific antigens or lymphokines could have adverse consequences if widely disseminated. It is therefore desirable to have a biological containment system regulated by the conditions that differ between the target environment and other environments, or which survives only temporarily in the target environment. In the case of microorganism-based delivery of recombinant expression products, it is desirable to have a microorganism that survives inside the animal, but dies outside of the animal, or which lives and survives inside the animal for sufficient time to induce an immune response, expose the animal to an expression product, and/or to deliver a transfer vector for production of an expression product within cells of the animal, prior to the onset of death within the animal. Live attenuated bacterial antigen delivery vectors with inherent biological containment features to preclude survival, proliferation and gene transfer in nature would increase the acceptability and enthusiasm for use of this type of antigen delivery microorganism.

It is therefore an object of the present invention to provide an Environmentally Limited Viability System for use in controlling viability of targeted microorganisms and limiting the undesirable survival of recombinant extrachromosomal genetic information if transferred to other microorganisms.

It is another object of the invention to provide a live recombinant microorganism with environmentally limited viability that can deliver an expression product or vector to a host organism or other environment.

It is another object of the invention to provide a method of delivering an expression product or vector to a host organism or other environment using a live recombinant microorganism with environmentally limited viability.

It is another object of the invention to provide a live recombinant antigen delivery microorganism with environmentally limited viability.

It is a further object of the invention to provide a method of vaccination using a live recombinant antigen delivery microorganism with environmentally limited viability.

SUMMARY OF THE INVENTION

Disclosed is an Environmentally Limited Viability System (ELVS) for microorganisms based on differences between permissive and non-permissive environments. Viability of the microorganisms are limited to a permissive environment by specifically expressing one or more essential genes only in the permissive environment, and/or expressing one or more lethal genes only in the non-permissive environment. Temporary viability in a non-permissive environment can be achieved by temporarily expressing one or more essential genes in a non-permissive environment, and/or temporarily delaying expression of one or more lethal genes in the non-permissive environment. Environmentally Limited Viability Systems are also disclosed involving coordinate expression of a combination of essential genes and lethal genes. Microorganisms containing an Environmentally Limited Viability System are useful for release into permissive and non-permissive environments. Temperature regulated Environmentally Limited Viability Systems and delayed death Environmentally Limited Viability Systems are particularly suited for delivery of expression products, such as antigens, using recombinant avirulent Salmonella by limiting their growth to the warmer environment inside the host, or by allowing growth for only a limited time in the host. Such microorganisms can be administered to protect humans or warm-blooded animals against bacterial, viral, mycotic and parasitic pathogens, especially those that colonize on or invade through mucosal surfaces. They can also be used for expression of gamete-specific antigens to induce immune responses to block fertilization, or to induce immune responses to tumor antigens.

Examples of Environmentally Limited Viability Systems are disclosed, including preferred forms involving viability limited by temperature and temporary viability in a non-permissive environment.

BRIEF DESCRIPTION OF THE DRAWINGS

FIGS. 10a, 10b, 10c and 10d are diagrams of an arabinose regulated Environmentally Limited Viability System. A plasmid based arabinose regulation system produces the C2 repressor responsible for the repression of either chromosomally or plasmid encoded lysis genes. The diagram indicates the increased amount of C2 repressor produced when the repressor gene is on a higher copy number plasmid. As with the system depicted in FIG. 9, the ratio of repressor to target determines the length of time prior to expression of the lysis genes. The use of a high copy-number repressor plasmid would increase the persistence of the strain in a non-permissive environment.

DETAILED DESCRIPTION OF THE INVENTION

Figures 1A, 1B:
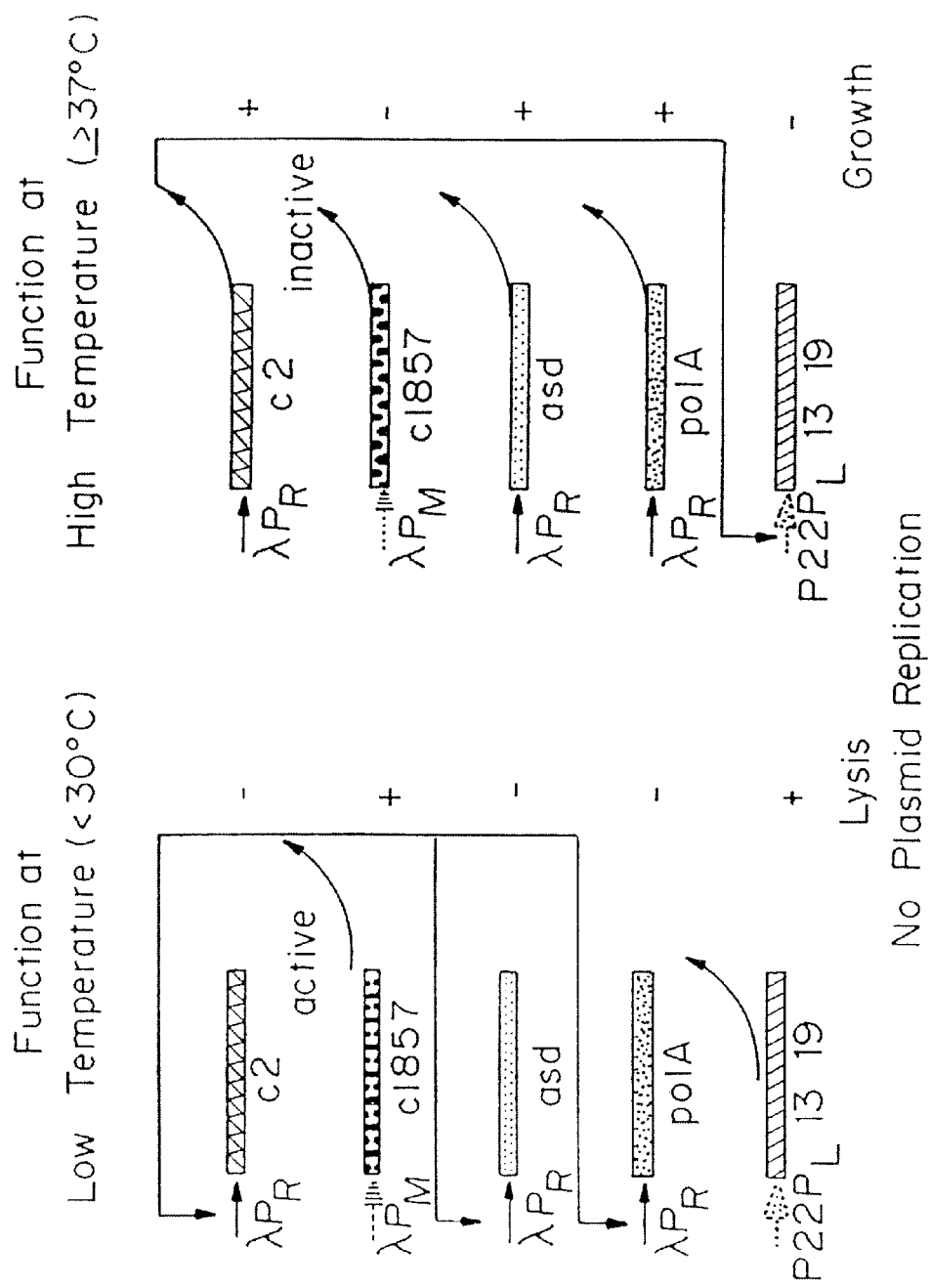
FIGS. 1*a* and 1*b* are diagrams of an Environmentally Limited Viability System including both plasmid encoded and chromosomally encoded elements. The diagram depicts the production of gene products as arrows pointing to a + for functional production at either low temperature (less than 30° C.) on the left, or high temperature (greater than 37° C.) on the right. The effects of chromosomally encoded C2 or CI857 repressors are depicted by the arrows pointing down at the respective promoters repressed by each repressor. The asd and lys13 lys19 genes are located on a plasmid with a polymerase I dependent replicon, providing expression of the lethal lysis genes at low temperature while the essential asd gene fails as the chromosomally encoded polymerase I is no longer produced and the plasmid with the asd gene is not retained. The promoters and regulators depicted may be interchanged with other environmentally regulated systems as they are characterized.

There are two main components useful for a successful biological containment system. The first component consists of genes encoding products that are either essential or potentially fatal to the bacterial cells containing them. The second component is a regulatory system to turn the critical genes on or off at the appropriate time. The challenge presented by a containment system for a live bacterial antigen delivery system is the recognition of an environmental trigger that will signal the death or a loss of viability of the cell after a defined period of time or upon release into a non-permissive environment, but will not prevent growth in a permissive environment.

The disclosed Environmentally Limited Viability System combines specific regulation with essential and/or lethal genes to limit the viability of a microorganism to a permissive environment, or for a limited time after transfer to a non-permissive environment. The Environmentally Limited Viability System can be combined with other mutations to limit the virulence of the bacterial host. A containment system encoding both essential and lethal gene products requires the cell to maintain the desired regulation or suffer either loss of an essential component or the effect of a lethal product. Any or all of the components of the Environmentally Limited Viability System can be located on a chromosome of the host microorganism, or located on an extrachromosomal element, such as a plasmid.

The Environmentally Limited Viability System makes use of genetically engineered host cells which can be maintained as a genetically stable population, wherein the host cells express a desired expression product. The host cells used for the Environmentally Limited Viability System contain environmentally regulated essential genes, lethal genes and/or replication genes. The expression of these genes is regulated to allow expression of the essential and replication genes only in a permissive environment, and expression of the lethal genes in non-permissive environments. Host cells used in the Environmentally Limited Viability System characteristically have an inactivated native gene encoding a gene essential for cell survival. A copy of this gene, which acts as an essential gene in the system, is placed on the vector of the system to provide selective pressure for maintenance of the vector.

The Environmentally Limited Viability System makes use of host cells adapted for use of the genetic components of the system. Vectors which are suitable for transforming the host cells, which contain the essential and lethal genes, and into which a gene encoding a desired polypeptide may be inserted, are also described. The disclosed Environmentally Limited Viability System is suitable for use for the production of desired polypeptides in industrial settings, for example, by growth in fermenters. For example, recombinant production of dangerous toxins can be performed with a reduced risk of escape by using an Environmentally Limited Viability System. Microorganisms incorporating the system may also be used as live antigen delivery microorganisms.

Genetic regulatory systems suitable for use in the Environmentally Limited Viability System are those that modulate gene expression based on environmental conditions, such as temperature, osmolarity, pH, oxygen availability, and the presence or absence of a nutrient or ion. A basic motif of many of these regulatory systems is an environmentally based change in a trans regulatory element that alters its interaction with a control sequence of the regulated gene. Such systems can be adapted to regulate the genes of the Environmentally Limited Viability System based on environmental changes that define a permissive and non-permissive environment.

As used herein, permissive environment refers to an environment in which microorganisms incorporating an Environmentally Limited Viability System are viable. Such an environment might possess a key characteristic, such as a specific temperature, osmolarity, pH, oxygen concentration or availability of a nutrient. As used herein, a non-permissive environment refers to an environment in which microorganisms incorporating an Environmentally Limited Viability System are non-viable or temporarily viable. As used herein, a non-viable cell or microorganism refers to a cell or microorganism that cannot grow. Viability is always considered relative to specific environments and environmental conditions. Thus, a cell can be considered non-viable in a particular environment even though the cell would be viable in other environments. As used herein, a temporarily viable cell or microorganism refers to a cell or microorganism that can remain viable for some limited period of time in a non-permissive environment. In the context of an Environmentally Limited Viability System, a temporarily viable cell or microorganism is temporarily viable in the non-permissive environment due to the temporary retention of intracellular conditions generated in the permissive environment. It is understood that the time for which temporarily viable cells or microorganisms remains viable in a non-permissive environment can depend on the specific Environmentally Limited Viability System and environment involved, and is not limited in any other way. It is not intended that the use of the term temporary be interpreted as limiting viability to any specific period of time; rather, temporary is intended to mean not permanent. Thus, temporary viability can refer to any impermanent period of viability in a non-permissive environment. It is also understood that cell death is considered a special form of non-viability.

It is preferred that the genes that make up an Environmentally Limited Viability System are modified or otherwise engineered to have the desired expression pattern. Specifically, it is preferred that ELVS genes be constructed by combining suitably regulated promoters with heterologous coding regions. Most of the examples herein describe and make use of such genetically engineered genes. As used herein, an ELVS gene where the gene, including any expression control sequences, has been altered from its naturally occurring structure such that expression of the gene is altered from its naturally occurring regulation is referred to as having engineered expression. For example, an essential gene under control of $P_{BAD}$, or a replication gene altered to be repressed by a lambda repressor are said to have engineered expression. On the other hand, genes for which the expression has not been altered by any alteration of the gene structure are not considered to have engineered expression. This is true even when, for example, the gene is controlled by the product of a regulatory gene the expression of which has been altered (that is, when such a regulatory gene has engineered expression). For example, a lambda repressor gene under control of its native promoter is not considered to have engineered control where the repressor gene has not been altered. Similarly, an intact essential gene under its normal expression control is not considered to have engineered expression, even if the location of the gene is altered by, for example, placing it on a vector. An example of a gene that does not have engineered control is an unaltered maltose catabolism gene placed on a vector. When such a vector is placed in a host lacking, or mutant for, the equivalent gene, the gene, under its natural expression regulation, will be expressed in the presence of maltose and not expressed in the absence of maltose. The identification of the maltose catabolism gene as not having engineered expression does not change even though the gene is "essential" to the host and even if environments containing and lacking maltose are defined as, or could be considered to be, permissive and non-permissive environments, respectively.

A. Essential Genes

The Environmentally Limited Viability System makes use of essential genes to limit cell viability and to provide selective pressure for maintenance of the vector component of the system. An essential gene, as used herein, refers to a gene required for cell viability. Containment is provided by regulating the essential gene, such that the gene is expressed in a permissive environment but is not expressed in a non-permissive environment.

As used herein, "gene" refers to a nucleic acid sequence having a coding sequence operatively linked to a control sequence. "Coding sequence" refers to a nucleic acid sequence encoding RNA or protein. The RNA or protein encoded by a coding sequence is referred to as an expression product. A coding sequence can encode one or more expression products. "Control sequence" refers to DNA sequences which are necessary to effect the expression of coding sequences to which they are operatively linked. Generally such control sequences include a promoter and ribosome binding site. The term "control sequence" is intended to include, at a minimum, all components whose presence is necessary for expression, and may also include additional components whose presence is advantageous, for example, operators, enhancers, and polyA signals. "Operatively linked" refers to a juxtaposition wherein the components so described are in a relationship permitting them to function in their intended manner. A control sequence operatively linked to a coding sequence refers to a control sequence associated with a coding sequence in such a way that expression of the coding sequence is achieved under conditions compatible with the control sequences.

The essential gene or genes can be located on an extrachromosomal vector or on a chromosome of the microorganism. Placing regulated essential genes on the chromosome provides stability for the genes and allows multiple essential genes to be combined in a single Environmentally Limited Viability System without increasing the size and complexity of the vector portion of the system. It is preferred, however, that at least one essential gene be expressed on the vector portion of the system in order to provide selection for plasmid maintenance.

The essential gene is also used to maintain the vector component of the Environmentally Limited Viability System in microorganisms of the system. This is important because most plasmids are maintained through the use of antibiotic selection and in many natural environments the use of antibiotics is unworkable or undesirable. Maintenance of plasmids in recombinant hosts when present in natural environments preferably use a different selection system. A preferred selection method involves a balanced-lethal host-vector system, where an essential gene is carried on a vector and the chromosomal gene is deleted, creating a balanced-lethal condition. The "lethal" deletion is balanced by the presence of the vector borne copy of the wild-type gene.

1. Genes essential for metabolism or growth. Most genes encoding enzymes involved in the metabolism or growth of a microorganism can be used as essential genes. All that is required is that the gene is regulated so that it is expressed only in a permissive environment. It is preferred that the essential gene be derived from a gene in the host microorganism. In many bacteria, expression of modification methylases are required to prevent endogenous restriction endonucleases from cleaving the host chromosome. Thus a modification methylase gene can also be used as the essential gene. Genes required for nucleic acid replication, such as genes encoding DNA ligase and gyrase, are essential for cell growth and can be used as the essential gene. Preferred essential genes are genes involved in purine biosynthesis, with purA being especially preferred. The use and effect of a purA mutation on Salmonella virulence is described by Sigwart et al., *Infection and Immunity* 57(6):1858–1861 (1989).

The gene encoding thymidylate synthetase (thyA) is also preferred as an essential gene. In the absence of thymine or thymidine, Thy$^-$ cells undergo thymidine-less death due to the degradation of their chromosome. The use of thyA mutants for this purpose is described in U.S. Pat. No. 4,190,495 to Curtiss and in U.S. Pat. No. 4,888,170 to Curtiss, both of which are hereby specifically incorporated by reference. The gene for RecA (recA) is also a preferred essential gene. RecA$^-$ mutants are avirulent and are very sensitive to UV light, X-rays, mutagens, and other DNA damaging agents. These mutants tend to undergo chromosome degradation and die. The combination of thyA and recA as essential genes in an ELVS is especially preferred.

2. Genes essential for cell wall or cell membrane integrity. All bacteria have a peptidoglycan layer of the cell wall which imparts shape and rigidity except mycoplasma. The peptidoglycan is made of a polymer of repeating muramic acid-N-acetylglucosamine and is cross-linked by short peptides. In all gram-negative bacteria and in Mycobacterium and Nocardia species of Eubacteria, the peptide is composed of L-alanine, D-glutamic acid, meso-diaminopimelic acid (DAP), and D-alanine. In most gram-positive microorganisms the DAP is replaced by its decarboxylation product L-lysine.

Enzymes which catalyze the biosynthesis of the cell wall component and its precursors are known in the art. For example, in the synthesis of peptidoglycans, the enzyme may be one which catalyzes the insertion of the cross-linking peptide, for example, D-alanyl-D-alanine ligase, or of the synthesis of the carbohydrate polymer, or it may be an enzyme which catalyzes a step in the biosynthesis of a precursor, for example, diaminopimelic acid (DAP). For a review of the biosynthesis of this family of amino acids, see Umbarger (1978). Examples of genes encoding enzymes which catalyze steps in the biosynthesis of DAP are known in the art for a variety of organisms, see, for example, *Genetic Maps* (O'Brien, ed., Cold Spring Harbor Laboratory, 1987), and include, for example, in *S. typhimurium* the dapA and dapB genes and for example, *E. coli,* the dapA, dapB, dapC, dapD, and dapE genes. Another enzyme which is essential for DAP synthesis is β-aspartate semialdehyde dehydrogenase (Asd), which is encoded by the asd gene. Publications describing DAP-related genes suitable for use in an Environmentally Limited Viability System include Cirillo, et al., *J Bacteriol* 176(14):4424–9 (July, 1994), Chen,et al., *J Biol Chem* 268(13):9448–65 (May 5, 1993), Degryse, *Mol Gen Genet* 227(1):49–51 (May, 1991), Maruyama, et al., *J Bacteriol* 170(8):3786–8 (August, 1988), Yeh, et al., *Mol Gen Genet* 212(1):105–11 (April, 1988), Mengin-Lecreulx, et al., *J Bacteriol* 170(5):2031–9 (May, 1988), Richaud, et al., *J Bacteriol* 169(4):1454–9 (April, 1987), Bouvier, et al., *J Biol Chem* 259(23):14829–34 (Dec. 10, 1984), Richaud, et al., *J Biol Chem* 259(23):14824–8 (Dec. 10, 1984), Moyed, et al.,*J Bacteriol* 155(2):768–75 (August, 1983), Sahm, et al., *Ann N Y Acad Sci* 782:25–39 (May 15, 1996), Collins, et al., *Int J Syst Bacteriol* 44(3):523–6 (July, 1994), Hourdou, et al., *Biochem J* 292(Pt 2):563–70 (Jun. 1, 1993), Curtiss, et al., *Res Microbiol* 141(7–8):797–805 (September-October, 1990), Roten, et al., *J Gen Microbiol* 137(Pt 4):951–62 (April, 1991), Degryse, *J Biotechnol* 18(1–2):29–39 (April, 1991), Serebrijski, et al., *J Bacteriol* 177(24):7255–60 (December, 1995), Galan, et al., *Gene* 94(1):29–35 (Sep. 28, 1990), Cardineau, et al., *J Biol Chem* 262(7):3344–53 (Mar. 5, 1987), Haziza, et al., *EMBO J* 1(3):379–84 (1982), Peredel'chuk, et al., *Mol Gen Mikobiol Virusol* (5–6):25–7 (May-June, 1992), Baril, et al., *J Gen Microbiol* 138(Pt 1):47–53 (January, 1992), Haziza, et al., *Biochimie* 64(3):227–30 (March, 1982), Rodriguez-Herva, et al.,*J Bacteriol* 178(6): 1699–706 (March, 1996), Young, et al.,*J Biol Chem* 270(51):30384–91 (Dec. 22, 1995), Rowland, et al., *Gene* 164(1):113–6 (Oct. 16, 1995), Begg, et al., *J Bacteriol* 177(21):6211–22 (November, 1995), Popham, et al.,*J Bacteriol* 177(16):4721–9 (August, 1995), Brown, et al., *J Bacteriol* 177(14):4194–7 (July, 1995), Buist, et al.,*J Bacteriol* 177(6): 1554–63 (March, 1995), Ho, et al., *Biochemistry* 34(8):2464–70 (Feb. 28, 1995), Evers, et al., *Gene* 140(1):97–102 (Mar. 11, 1994), Mengin-Lecrulx, et al., *J Bacteriol* 175(19):6150–7 (October, 1993), Doublet, et al.,*J Bacteriol* 175(10:2970–9 (May, 1993), Bouloc, et al., *EMBO* 8(1):317–23 (January, 1989), Walsh, *J Biol Chem* 264(5):2393–6 (Feb. 15, 1989), Dai, et al., *J Bacteriol* 170(5):2197–201 (May, 1988), Goodell, et al., *J Bacteriol* 169(8):3861–5 (August, 1987), Chakraborti,et al., *J Bacteriol* 168(3):1422–9 (December, 1986), Kusser, et al., *J Bacteriol* 164(2):861–5 (November, 1985), and Giam, et al., *J Biol Chem* 259(9):5601–5 (May 10, 1984).

The use of asd in an unregulated balanced-lethal system is described by (Nakayama et al., *Bio/Technology* 6:693–697 (1988)). This system uses plasmid vectors with the wild-type gene encoding the enzyme β-aspartate semialdehyde dehydrogenase required for the synthesis of DAP in conjunction with a Salmonella strain which has a chromosomal asd mutation. Since DAP is synthesized only by bacteria and is not present in the tissues of an immunized host, loss of the Asd$^+$ vector from the recombinant avirulent Salmonella leads to death and lysis of the bacterial cell (Nakayama et al. (1988)). In the disclosed Environmentally Limited Viability System, the asd balanced-lethal system can be adapted by regulating the expression of the essential asd gene.

Accordingly, a preferred essential gene is asd, encoding β-aspartate semialdehyde dehydrogenase, an enzyme required for the synthesis of an essential component of the rigid layer of the bacterial cell wall, namely diaminopimelic acid (DAP). DAP is only synthesized by bacteria and is not prevalent in the environment. DAP is synthesized in six enzymatic steps from β-aspartate semialdehyde, which, in turn, is synthesized in two steps from L-aspartic acid. In the first step, L-aspartic acid is phosphorylated by one of several (usually three) β-aspartokinases which are encoded by several (usually three) separate genes regulated independently by repression and/or feedback inhibition of the gene products by the ultimate end products L-threonine, L-methionine, and L-lysine. β-aspartophosphate is converted in one step to β-aspartic semialdehyde by β-aspartic semialdehyde dehydrogenase, the product of the asd gene. Mutants with a point mutation in or deletion of the asd gene as well as mutants with mutations in any of the six genes specifying the enzymes for converting β-aspartate semialdehyde to DAP have an obligatory requirement for DAP in all media. When DAP-requiring mutants are deprived of DAP, they die and are lysed, releasing their contents.

The gene for β-aspartate semialdehyde dehydrogenase from *Streptococcus mutans* PS 14 (UAB62) has been cloned and expressed in asd mutants of *E. coli,* as described by Jagusztyn-Krynicka et al. (1982), and Curtiss et al. (1982). Subsequently, the *S. mutans* asd gene was sequenced by Cardineau and Curtiss (1987). The cloning and mutation of the asd gene of *S. typhimurium* is described by Galan et al., *Gene* 94:29–35 (1990).

In both gram-positive and gram-negative bacteria, the peptide cross-linking repeating muramic acid-N-acetylglucosamine polymers contain D-alanine. D-alanine is synthesized from L-alanine by alanine racemase, the product of the dal gene (*B. subtilis*), and then is converted to a D-alanyl-D-alanine dipeptide by the enzyme D-alanyl-D-alanine ligase, the product of the ddl gene. D-alanine is coupled to the L-alanyl D-glutamyl DAP or L-alanyl-D-glutamyl-L lysine tripeptide which is attached to one muramic acid-N-acetylglucosamine polymer to form a pentapeptide. The terminal D-alanine is then cleaved during the enzymatic cross-linking reaction to the next muramic acid-N-acetylglucosamine polymer. Mutants of *Bacillus subtilis* lacking the ability to synthesize D-alanine or to synthesize D-alanyl-D-alanine lyse in media devoid of D-alanine or of the dipeptide. dal mutants of *B. subtilis* lacking alanine racemase have been isolated (Ferrari et al., *Bio/Technology* 3:1003–1007 (1985); Dul et al. (1973)). ddl mutants lacking D-alanyl D-alanine ligase have been isolated in *E. coli* (Wijsman (1972), Miyakawa et al. (1972), Lugtenberg et al. (1973)) and in *B. subtilis.* As in the case of the asd and dap mutations, the inclusion of dal and/or ddl mutations in strains of bacteria limits the viability of the organisms, since such mutant strains are unable to survive in environments other than a carefully controlled laboratory environment.

Lipid polysaccharides (LPS) are important structures on the surface of many bacteria (Raetz, *Escherichia coli and Salmonella typhimurium Cellular and Molecular Biology,* Vol. I (ASM Press, Washington, D.C., Neidhart et al., eds., 1996) pages 1035–1057). If LPS is not properly formed, the viability of the cell can be greatly reduced. Accordingly, genes involved in the synthesis of LPS can be used as essential genes. A preferred set of genes of this type are the lpx genes (also variously known as firA, ssc, and omsA; Vuorio and Vaara, *J. Bacteriol.* 174(22):7090–7097 (1992), Helander et al., *Eur. J. Biochem.* 204:1101–1106 (1992), Hirvas et al., *EMBO J.* 10(4):1017–1023 (1991)), which are involved in the synthesis of the lipid A moiety of LPS. These genes encode the enzyme UDP-3-O-(R-3-hydroxymyristoyl)-glucosamine N-acyltransferase.

The O-antigen and outer core of lipopolysaccharides can also be altered to make the strains less viable. Such cells will be less likely to survive in nature than a smooth Salmonella with wild-type levels of LPS. Mutation in either of two genes, galE or pmi, has the potential of conferring this phenotype on Salmonella. This effect can be used in an Environmentally Limited Viability System by, for example, mutating the pmi and/or galE gene present in the host cell. The pmi and/or galE gene can also be operatively linked to a regulated promoter and placed on the chromosome or into a low copy numbered plasmid as part of an ELVS. This will result in LPS synthesis that will be "normal" for some number of generations of growth in a non-permissive environment. Eventually the strain will become rough and display enhanced susceptibility to killing by non-specific host defense mechanisms. Such rough strains also survive less well in environments outside of animal bodies, such as in soil.

The galE gene encodes UDP-galactose epimerase, which interconverts UDP-galactose with UDP-glucose, and permits cells grown on glucose to make UDP-galactose which is a precursor both for the LPS core and the O-antigen side chain in Salmonella. In the absence of galactose, strains with a mutation in the galE gene are unable to synthesize UDP-galactose; therefore, they are unable to synthesize LPS and are rough, totally avirulent (Germanier and Furer (1971)), unable to invade through the mucin and glycocalyx lining the intestinal tract, and are extremely susceptible to nonspecific host defense mechanisms. galE mutants only make UDP-galactose when supplied with exogenous galactose. In mammalian cells it appears that most galactose is in a modified form (for example, phosphorylated) that cannot be utilized by bacteria. Therefore, it is anticipated that in animals, a galE mutant would not make normal LPS, due to an insufficiency of galactose.

The pmi gene encodes phosphomannose isomerase, which interconverts fructose-6-phosphate with mannose-6-phosphate. Growth of a pmi mutant in the presence of mannose allows normal synthesis of the Salmonella O-antigen side chain, whereas cultivation in any medium laking mannose leads to the absence of the O-antigen side chain but a normal core polysaccharide. Moreover, the remaining core in pmi mutants is very similar to those of all enterics; therefore, an antibody response against this component of core may induce immune responses that are more cross-protective against infections due to diverse Salmonella serotypes and to other enterics (that is, members of the Enterobacteriaceae).

The rfc gene encodes O-antigen polymerase, which polymerizes multiple O-antigen repeats to make O-antigen chains. The rfc gene can be used as an essential gene since a normal polysaccharide coat will not be synthesized when it is not expressed.

All microorganisms have a cell membrane that retains the cytoplasmic contents. During growth, new membrane components must be synthesized to maintain the integrity of increased surface area of the membrane on the growing cell. Critical genes involved in metabolism of cell membrane components can be used for the essential gene. Such genes include genes involved in fatty acid biosynthesis (fab), fatty acid degradation (fad), phospholipid synthesis (pls), and phospholipases.

B. Lethal Genes

Regulated lethal genes are used in the Environmentally Limited Viability System to actively kill host cells that escape to a non-permissive environment or after some limited growth in a host. A lethal gene, as used herein, refers to a gene that is lethal to the host microorganism when expressed. A regulated lethal gene which is repressed in the permissive environment, but expressed in the non-permissive environment, acts as a positive containment mechanism for the Environmentally Limited Viability System. It is intended that a lethal gene can cause cell death by direct action of the gene product of the lethal gene, indirectly by regulating the expression of other genes that cause cell death, or by both direct and indirect action. Where multiple genes are involved in causing the death of the cell, all of the genes in this cascade can be considered lethal genes. In such cases, the first gene in the expression cascade is referred to as the primary lethal gene. Unless otherwise stated, the term lethal gene refers only to the primary lethal gene. It is preferred that only the primary lethal gene, in a cascade of lethal genes, be regulated for expression in the non-permissive environment.

Lethal genes useful in the Environmentally Limited Viability System include cell-killing gene products of the gef gene family that form holes in cell membranes when over-produced. Some of these host killing genes, such as hok, are plasmid derived and ensure that plasmid-free cells do not survive (Gerdes et al., *Proc. Natl. Acad. Sci, USA* 83:3116–3120 (1986)). Others, such as gef and relF, are of chromosomal origin with unclear functions (Poulsen et al., *Mol. Microbiol.* 5:1639–1648 (1991), Gerdes et al., *EMBO J.* 5:2023–2029 (1986), Gerdes et al., *New Biol.* 2:946–956 (1990)). Other bacterial host killing gene products useful as lethal genes include nucleases (Molin et al., *Annu. Rev. Microbiol.* 47:139–166 (1983)), phospholipases (Givskov et al., *J. Bacteriol.* 170:5855–5862 (1988)), plasmid maintenance genes (Figurski et al. (1982)), and colicin genes, such as colE3 (Munthali et al., *App. Environ. Microbiol.* 62(5):1805–1807 (1996)). A useful nuclease gene is pvuR (Tao and Blumenthal, *J. Bacteriol.* 174(10):3395–3398 (1992)). Useful endolysins and holins of the bacteriophages lambda (Bienkowska-Szewczyk et al., *Mol. Gen. Genet.* 184:111–114 (1981), Reader and Siminovitch, *Virology* 43:623–637 (1971)) and P22 (Rennell and Poteete, *Virology* 143:280–289 (1985)) are also available. Their expression forms lesions in the bacterial inner membrane with subsequent degradation of the cell wall and release of cytoplasmic contents (Young, *Microbiol. Rev.* 56:430–481 (1992)). Publications describing additional lethal genes suitable for use in an Environmentally Limited Viability System include Harkness, et al., *J Bacteriol* 172(1):498–500 (January, 1990), and Bienkowska-Szewczyk, et al., *Mol Gen Genet* 184(1): 111–4 (1981). Preferred lethal genes are the combination of bacteriophage P22 lysis genes 13 and 19, coding for a porin and lysozyme, respectively. The joint action of these two proteins leads to production of holes in the cell membrane and degradation of the bacterial cell wall.

A gene encoding a tRNA (including a suppressor tRNA), or a tRNA that would have acceptor activity but a wrong codon to cause synthesis of mutant proteins, could also be used as a lethal gene. A nuclease active against DNA or mRNA could also be lethal when overexpressed.

The lethal gene may be located on a chromosome of the host microorganism or an extrachromosomal element. One advantage of locating lethal genes on a vector is to limit the amount of growth during which an inactivating mutation could occur. For Environmentally Limited Viability Systems not involving delayed death, it is preferred that the lethal gene be placed on an extrachromosomal vector regulated by a chromosomally expressed negative trans regulatory element. With this arrangement, should the plasmid be transferred to another microorganism, the lethal gene will be expressed constitutively and lead to the demise of that recipient cell. Thus, the Environmentally Limited Viability System will prevent both survival and spread of the recombinant strain within the environment and transmission of recombinant plasmids within natural populations of bacteria. Preferred arrangements of the elements in a delayed death Environmentally Limited Viability System are discussed below.

Cell death caused by phage lysis. Special forms of lethal genes are the genes responsible for prophage excision. In an Environmentally Limited Viability System, such genes can be used as primary lethal genes in a cascade making use of the normal excision and lysis machinery of a phage. Use of a modified prophage with a properly regulated excision gene will cause the death of a lysogenic bacteria in vivo by lysis from within. This form of Environmentally Limited Viability System which causes explosive death of the cell is referred to as an Alien system. The idea is to contain within the chromosome a prophage specifying normal functions for excision of the prophage from the chromosome and for lysis of the cell, but without the ability to form mature infectious phage particles. Such a prophage can be constructed by, for example, deleting one or more of the genes necessary for assembly of phage heads and/or tails. In this system, when the lethal genes, encoding phage proteins for prophage excision, are expressed, the prophage is excised, and lysis of the bacterial host cell ensues, but no infectious viral particles are produced. In this system, the lysis machinery of a prophage is the agent of cell death, while the excision of the prophage is the regulated event. Regulation of prophage excision is preferably accomplished by regulation of the natural repressor of prophage excision. Thus, by expressing the repressor gene in the permissive environment, and preventing expression in the non-permissive environment, excision of the prophage (and thus cell lysis) will be limited to the non-permissive environment. Such a system can allow some growth prior to prophage excision and lysis by employing a delayed death Environmentally Limited Viability System.

A preferred form of regulation of the prophage excision genes (primary lethal gene) in an Alien system is the gradual loss of a repressor that regulates these genes. This can be accomplished by supplying an inducer for the gene encoding a repressor regulating the primary lethal gene during growth of the cell strain (in a fermenter, for example). When the inducer is no longer provided, such as when the cells are administered to a host, the concentration of inducer gradually declines and the repressor is no longer made. The concentration of repressor can then also gradually decline. The ultimate result is the loss of repression of the prophage excision genes, whereupon the prophage is excised and lysis ensues. As an example, a Salmonella strain could have the P22 c2 gene under the control of the araC-$P_{BAD}$ system (which is described below). This element could be on a moderate to high copy number plasmid, inserted into a virulence plasmid, or introduced into the chromosome. By providing arabinose during growth of the strain, the Salmonella will take up the arabinose, the P22 C2 repressor will be produced, and the prophage will remain stably integrated into the chromosome. Once the strain is placed in a host, where arabinose is unlikely to be present, the expression of the $P_{BAD}$ controlled c2 gene will cease, so that the c2 gene product decreases in concentration either due to breakdown or to dilution resulting from growth and cell division. At some point the level of c2 gene product will be insufficient to repress transcription of phage genes leading to excision, replication and cell lysis.

The above system can be constructed by operatively linking araC-$P_{BAD}$ to the P22 c2 gene to generate a cartridge that can be inserted into, for example, the chromosome or a Salmonella virulence plasmid or a multi-copy plasmid replicon. Once such a Salmonella strain is constructed, then the strain can be infected with a P22 c2 mutant or a c1 c2 double mutant to create a lysogenized strain. The delayed effect of transfer from a permissive environment to a non-permissive environment can be easily measured by monitoring the loss of colony forming units during growth in a non-permissive environment (in this case, in the absence of arabinose).

Essentially all bacterial species are lysogenic for one or more phages and such prophages can be adapted for use in systems causing cell lysis according to the principles described above. In this way, Alien systems can be used with bacterial hosts in general.

C. Replication Genes

Biological containment of the Environmentally Limited Viability System can be enhanced by regulating the expression of a replication gene. A replication gene, as used herein, refers to a gene required for replication of an extrachromosomal vector. Use of a properly regulated replication gene reinforces the dependence of the cell on an essential gene by placing the vector containing the essential gene into a host with a gene required for the replication and maintenance of that vector. A preferred replication gene is polA, encoding DNA polymerase I, an enzyme required for replication of a number of plasmid replicons. The failure of the host cell to synthesize DNA polymerase I will halt plasmid vector replication and progeny cells will be formed lacking the plasmid containing the essential gene, thus resulting in non-viable cells (Kingsbury et al., *J. Bacteriol.* 114:1116–1124 (1973)).

It is preferred that the environmentally regulated replication gene be placed on a chromosome of the host microorganism.

1. Replication Dependent On Suppression. Replication of a vector that is part of an Environmentally Limited Viability System can also be made dependent on the presence of a suppressor gene. Such an arrangement would limit the ability of the vector to be effectively replicated or maintained if it is transferred to another host. Preferably this can be accomplished by including an amber codon in a gene on the vector involved in replication or maintenance of the vector. It is also required that the intended host include a suppressor gene on the chromosome. When such a scheme is used, the vector is replicated and maintained in the ELVS host since the chromosomally-based suppressor gene allows expression of the vector-based gene having an internal amber codon, but is not replicated or maintained in another host (if it is transferred) since the new host will not have the required suppressor gene. This last point is expected since it has been shown that, for example, fewer than 0.5% of *E. coli* strains isolated from diverse natural sources have amber suppressors (Robeson et al., *Nature* 283:104–106 (1980)).

2. Runaway Replication. Replication of plasmids in an Environmentally Limited Viability System can also be regulated to allow runaway replication. Such runaway replication is especially useful in delayed death Environmentally Limited Viability Systems where maximum expression of an expression gene in a non-permissive environment is desired prior to the onset of death.

The amount of expression product produced by a cell is proportional to gene copy number in addition to promoter strength. While it is desirable to deliver the maximum amount of some expression products to certain environments, using an Environmentally Limited Viability System, some expression products are deleterious to the microorganisms used. Containment systems employing lethal genes also can potentially produce deleterious effects on the microorganism if present at high copy number without tight regulation. These conflicting goals can be reconciled by employing a regulated plasmid replication system which provides a low copy number during growth in the permissive environment and early in the colonization of the non-permissive environment followed by a rapid increase in copy number as the high copy number replicon is activated. This system would then culminate in excessive expression of both the expression product and the lethal gene.

Figures 8A, 8B:
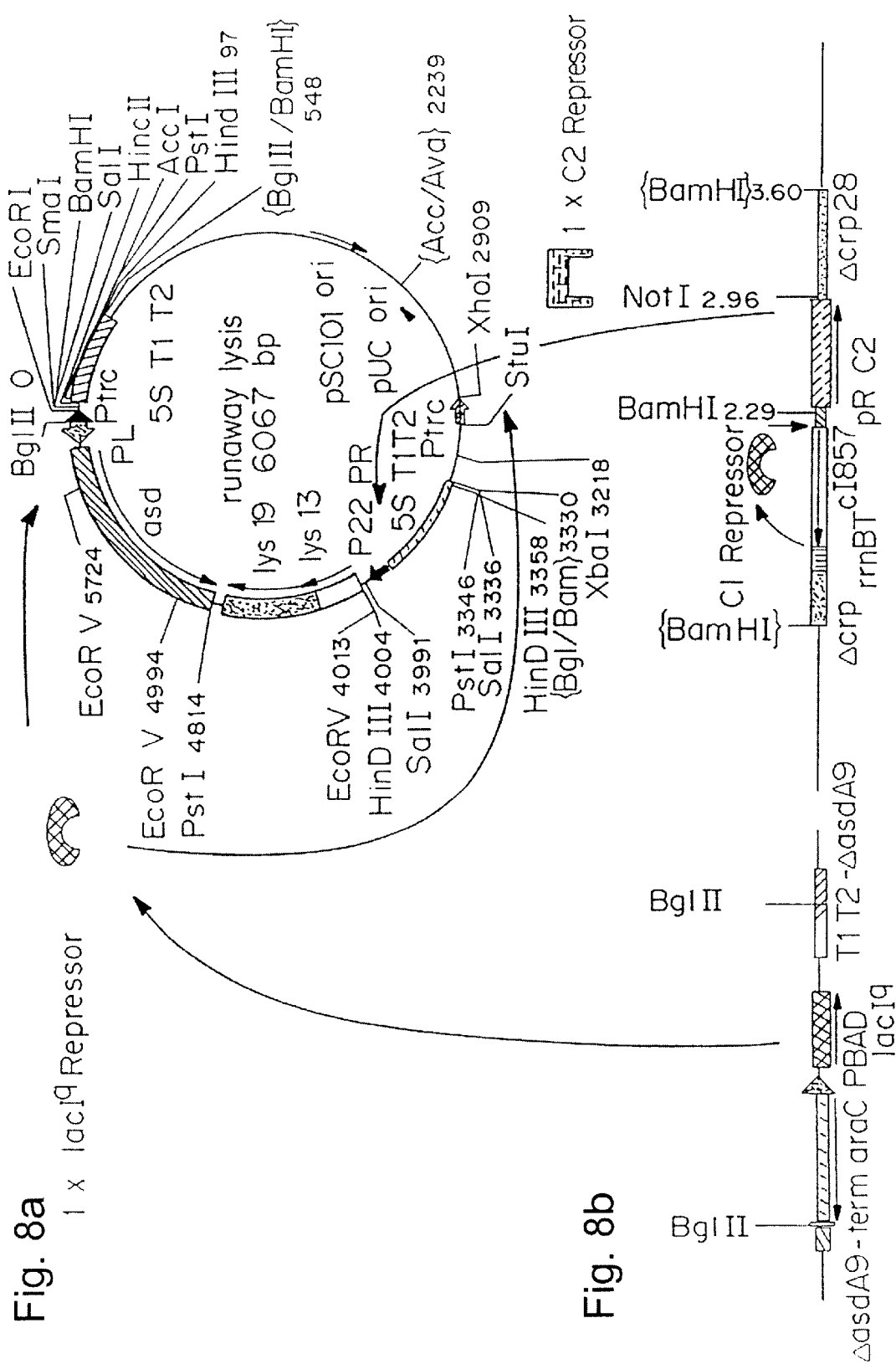
FIGS. 8a and 8b are diagrams of an Environmental Limited Viability System utilizing a runaway plasmid containing lethal lysis genes. The mechanism responsible for the runaway plasmid effect is the use of a pUC origin of replication with the promoter for the primer of replication replaced by the LacI repressed trc promoter. Production of LacI is governed by araC-$P_{BAD}$ in a cassette inserted into the chromosomal asd gene. In the presence of arabinose, the LacI produced will prevent expression of the trc promoter resulting in the low (6 to 8 copies/chromosome) plasmid copy-number being determined by the pSC101 replicon. During growth of the strain at temperatures greater than 37° C. the temperature-sensitive CI857 repressor will fail to shut off expression of C2 on the chromosome and C2 will then prevent expression of the plasmid borne lys13 lys19 lethal genes. Upon introduction of the strain into an environment lacking arabinose, no more LacI repressor will be made and the $P_{trc}$ driven pUC replicon will predominate, driving the plasmid copy-number beyond 300 copies per chromosome, far exceeding the C2 repressor levels and thus overexpressing the lysis genes. Furthermore, if the strain is released into an environment of 30° C. or less, CI857 will effectively shut down expression of C2 and thus cause a further enhancement in the expression of the lysis genes.

An example of an Environmentally Limited Viability System with a regulated plasmid replication system is shown in FIG. 8. The core of this ELVS is a plasmid containing two different origins of replication, a low (6 to 8 copies per chromosome) copy number pSC101 replicon and a regulated high (greater than 300 copies per chromosome) copy number pUC replicon. The regulation of the pUC replicon is obtained by replacing the promoter for the primer of replication with a LacI regulated promoter such as $P_{trc}$. While the trc promoter is repressed, the pUC origin of replication does not function and the dual replicon plasmid is maintained at the low copy number dictated by the pSC101 replicon. Upon loss of the LacI repressor, the pUC origin of replication dominates and the plasmid copy number increases to 300 copies per chromosome (Yarrington et al., *Gene* 28:293–300 (1984)). The regulatory mechanism responsible for the ELVS is composed of two components located on the chromosome, a positive regulatory promoter, such as araC-$P_{BAD}$ which is activated in the presence of arabinose, and an effective repressor such as LacI. The runaway replication plasmid would not only have an expression gene of interest (not shown in FIG. 8), but also contain lethal genes such as the lysis genes, lys13 lys19 of the bacteriophage P22, regulated by a chromosomally located C2 repressor expressed by the temperature regulated $\lambda P_R$ (as shown in FIG. 8) or by araC-$P_{BAD}$. The presence of the C2 repressor produced in the permissive environment of temperatures above 30° C. (as indicated in FIG. 8) or in the presence of arabinose would prevent expression of the lethal genes while plasmid copy number is low. However, upon encountering a non-permissive environment, such as one lacking arabinose (as indicated in FIG. 8), the plasmid copy number would increase beyond the level of C2 repressor and the lysis genes would be expressed. The loss of the LacI repressor would also allow expression of the gene of interest with product levels increasing as the plasmid copy number increases, until the cell begins to die due to the production of the lysis proteins. The essential asd gene depicted in FIG. 8 is regulated by the temperature-sensitive CI857 repressor and would be on at temperatures above 37° C., at both low and high copy number, but would be repressed at temperatures below 30° C. The inability of the CI857 repressor to shut off expression of the C2 repressor at high temperature would then prevent expression of the lethal lysis genes while growing at temperatures of 37° C. or above within a fermenter and within the host while plasmid copy number is low. Copy number is kept low in the presence of arabinose since expression of the $LacI^q$ repressor is driven by araC-$P_{BAD}$, and the $LacI^q$ repressor in turn is required to prevent expression from $P_{trc}$ driving the pUC primer of replication. The $LacI^q$ repressor also represses the expression of an expression gene cloned into the MCS downstream from $P_{trc}$. Transfer of the cells to an environment without arabinose results in the cessation of $LacI^q$ production and continued growth of the cells would gradually reduce the concentration of $LacI^q$ repressor available in the cell, allowing expression of the pUC primer of replication and transcription of the sequence encoding the foreign antigen.

The continued growth of the cells in an environment without arabinose would result in the rapid increase in plasmid copy number once the $LacI^q$ repressor level decreased to a level allowing expression from $P_{trc}$. The increasing plasmid copy number would then be followed by high-level expression of the expression product along with increasing levels of the lysis gene product as plasmid copy number exceeded C2 repressor levels produced by the chromosomally encoded C2 repressor.

Runaway replication can be accomplished by regulating expression of the primer of a pUC origin of replication using control systems described for use with essential or lethal genes. It is preferred that the origin of replication primer is regulated to be expressed only in the non-permissive environment. It is also preferred that runaway replication be used as a part of or in conjunction with delayed death Environmentally Limited Viability Systems. This allows maximum production of expression products and can be used to increase the effectiveness of lethal genes carried on the runaway replication plasmid.

D. Regulatory Elements

The three categories of genes described above (essential, lethal, and replication) require a regulatory system that ensures viability in the permissive environment and death and lysis in the non-permissive environment. Regulation is coordinated and maintained using control sequences either directly linked to the essential, lethal, and replication genes of the Environmentally Limited Viability System, or linked to coding sequences encoding trans regulatory elements that modulate the expression of the genes of the Environmentally Limited Viability System. The switch in expression is mediated by environmentally based changes in trans regulatory elements. In general, the genes of the Environmentally Limited Viability System can be regulated 1) by linking the coding sequences to control sequences that promote or prevent transcription in the permissive and non-permissive environments, 2) by regulating the expression of trans regulatory elements that in turn promote or prevent transcription of the genes of the Environmentally Limited Viability System, 3) by adapting or altering trans regulatory elements, which act on the genes of the Environmentally Limited Viability System, to be active or inactive in either the permissive or non-permissive environment, or using combinations of these schemes. The Environmentally Limited Viability System requires the use of various promoters to coordinate expression of different elements of the system. Some elements, such as temperature-sensitive repressors or environment-specific regulatory elements, use constitutive promoters. Preferred promoters for use as regulatory elements in an Environmentally Limited Viability System are the cspA gene promoter, the phoA gene promoter, $P_{BAD}$ (in an araC-$P_{BAD}$ system), the trp promoter, the tac promoter, the trc promoter, $\lambda P_L$, P22 $P_R$, mal promoters, and the lac promoter. These promoters mediate transcription at low temperature, at low phosphate levels, in the presence of arabinose, in the presence of at low tryptophan levels, and in the presence of lactose (or other lac inducers), respectively. Each of these promoters and their regulatory systems are well known.

1. Trans Regulatory Elements. As used herein, trans regulatory element refers to a molecule or complex that modulates the expression of a gene. Examples include repressors that bind to operators in a control sequence, activators that cause transcription initiation, and antisense RNA that binds to and prevents translation of a mRNA. For use in Environmentally Limited Viability Systems, expression from regulated promoters is modulated by promoter regulatory proteins. These promoter regulatory proteins can function to activate or repress transcription from the promoter. Preferred trans regulatory elements are proteins mediating regulation of the cspA gene promoter, the phoA gene promoter, $P_{BAD}$ (in an araC-$P_{BAD}$ system), the trp promoter, the tac promoter, the trc promoter, the mal promoters, and the lac promoter.

Another type of trans regulatory element is RNA polymerase. Genes of the Environmentally Limited Viability System can be regulated by linking them to promoters recognized only by specific RNA polymerases. By regulating the expression of the specific RNA polymerase, expression of the gene is also regulated. For example, T7 RNA polymerase requires a specific promoter sequence that is not recognized by bacterial RNA polymerases. A T7 RNA polymerase gene can be placed in the host cell, regulated to be expressed only in the permissive or non-permissive environment. Expression of the T7 RNA polymerase will in turn express any gene linked to a T7 RNA polymerase promoter. A description of how to use T7 RNA polymerase to regulate expression of a gene of interest, including descriptions of nucleic acid sequences useful for this regulation appears in Studier et al., *Methods Enzymol.* 185:60–89 (1990).

Another type of trans regulatory element is antisense RNA. Antisense RNA is complementary to a nucleic acid sequence, referred to as a target sequence, of a gene to be regulated. Hybridization between the antisense RNA and the target sequence prevents expression of the gene. Typically, antisense RNA complementary to the mRNA of a gene is used and the primary effect is to prevent translation of the mRNA. Expression of the genes of the Environmentally Limited Viability System is regulated by controlling the expression of the antisense RNA. Expression of the antisense RNA in turn prevents expression of the gene of interest. A complete description of how to use antisense RNA to regulate expression of a gene of interest appears in U.S. Pat. No. 5,190,931.

Other types of trans regulatory elements are elements of the quorum sensing apparatus. Quorum sensing is used by some cells to induce expression of genes when the cell population reaches a high density. The quorum sensing system is activated by a diffusible compound that interacts with a regulatory protein to induce expression of specific genes (Fuqua et al., *J. Bateriol.* 176:269–275 (1994)). There is evidence that the diffusible compound, referred to as an autoinducer, interacts directly with a transcriptional activator. This interaction allows the activator to bind to DNA and activate transcription. Each quorum sensing transcriptional activator is typically activated only by a specific autoinducer, although the activator can induce more than one gene. It has also been shown that quorum sensing regulation requires only the transcriptional activator and a gene which contains a functional binding site for the activator (Gray et al., *J. Bacteriol.* 176:3076–3080 (1994)). This indicates that quorum sensing regulation can be adapted for the regulation of genes in an Environmentally Limited Viability System. For example, a gene encoding a quorum sensing transcriptional activator can be expressed in an ELVS host, and another gene of the ELVS can be under the control of a promoter that is controlled by the quorum sensing transcriptional activator. This will cause the ELVS gene to be expressed when the cognate autoinducer is present and not expressed in the absence of the autoinducer. An ELVS gene under such control is referred to herein as being under quorum control. Where the ELVS host produces the autoinducer, the ELVS gene under quorum control will be expressed when cell density is high, and will not be expressed when cell density is low. Any of the genes in an ELVS can be placed under quorum control, including essential genes, lethal genes, replication genes and regulatory genes. For operation of the ELVS, the autoinducer can be supplied, for example, by the ELVS host through the action of endogenous genes (that is, genes responsible for the synthesis of the autoinducer), in the medium in a fermenter, or both. In the later case, the autoinducer supplied in the medium mimics the permissive conditions of high cell density. Alternatively, a gene for the production or synthesis of the autoinducer can be incorporated as an element of an ELVS. Such an autoinducer gene would be considered a regulatory gene as used herein.

Examples of quorum sensing transcriptional activator genes and genes for the production of their cognate autoinducer are luxR and luxI (Gray et al.), lasR and lasI (Gambello and Iglewski, *J. Bacteriol.* 173:3000–3009 (1991)), traR and traI (Piper et al., *Nature* 362:448–450 (1993)), rhlI and rhlR (Latifi et al., *Mol Microbiol* 17(2): 333–343 (1995)), and expR and expI (Pirhonen et al., *EMBO J* 12:2467–2476 (1993)). Autoinducers for these pairs include N-(3-oxohexanoyl)homoserine lactone (VAI; for LuxR), N-(3-oxododecanoyl)homoserine lactone (PAI; for LasR), and N-(3-oxo-octanoyl) homoserine lactone (AAI; for TraR). Some promoters that are induced by the quorum sensing transcriptional activators are luxI promoters, the lasB promoter, the traA promoter, and the traI promoter.

Quorum control can be used to effect environmentally limited viability in a number of ways. This can be accomplished, for example, by obtaining expression of essential genes and/or replication genes, and non-expression of lethal genes under permissive conditions of high cell density in, for example, a fermenter, with the opposite expression pattern appearing as cell density decreases when, for example, the cells are introduced into an animal or released into the environment. As another example, a regulatory gene such c2 can be placed under quorum control. Then other elements of the ELVS can be placed under control of the product of the regulatory gene, using, for example, $P22P_R$. The regulatory gene will be expressed in the presence of the autoinducer, and not expressed in the absence of the autoinducer. Where the regulatory gene is c2 and an ELVS gene is linked to $P^{22}P_R$, the ELVS gene will be expressed (that is, derepressed) when the autoinducer is not present (since no C2 protein will be made), and repressed when the autoinducer is present. Where an essential gene or a replication gene is under quorum control (the autoinducer induces expression), it is preferred that the autoinducer be present in the permissive environment and absent in the non-permissive environment. Where a lethal gene is under quorum control (the autoinducer induces expression), it is preferred that the autoinducer be present in the non-permissive environment and absent in the permissive environment. Where a regulatory gene is under quorum control, the presence or absence of the autoinducer in the permissive or non-permissive environment will depend on whether the product of the regulatory gene is a positive or negative regulator and whether the regulator is controlling the expression of an essential gene, a replication gene, or a lethal gene.

Trans regulatory elements, such as repressors or antisense RNA, can be expressed from either the chromosome or a plasmid. To limit the size and complexity of the plasmid portion of the system, however, it is preferred that these regulatory elements be expressed from the bacterial chromosome.

2. Temperature-Sensitive Regulation. A preferred type of regulation for microorganisms intended for growth in humans or warm-blooded animals is temperature regulation. This is based on the contrast between the high and constant body temperature present in mammals and birds and the low and variable temperature present in the ambient environment into which microorganisms are shed. To accomplish this, a preferred Environmentally Limited Viability System expresses genes ensuring survival at about 37° C. and prevents expression of genes that would cause death or lysis at about 37° C. It is preferred that, where an Environmentally Limited Viability System is intended to be administered to an animal, any temperature-based regulation should take into account the normal body temperature of the target animal. For example, chickens have a body temperature of 41.5° C., and pigs have a body temperature of around 40° C. The system can be designed so that at about 30° C. or below, the genes needed for survival cease to be expressed and genes that actively cause cell death and lysis are expressed at high level. This can be accomplished. by using promoters and regulatory elements that are regulated by temperature, or by adapting other regulatory systems to function in a temperature-dependent manner.

Temperature-regulated gene expression suitable for use in the Environmentally Limited Viability System are described by (Neidhardt et al., *Annu. Rev. Genet.* 18:295–329 (1984)). There are well-defined heat shock genes (Neidhardt et al. (1984)) that are well expressed at high temperature. Although the expression of these genes is temperature-regulated, there is frequently some low basal level of expression at the restrictive temperatures (Jones et al., *J. Bacteriol.* 169:2092–2095 (1987)). Temperature-regulated promoters exhibiting tighter control are described by Tobe et al., *Mol. Micro.* 5:887–893 (1991), Hromockyi et al., *Mol. Micro.* 6:2113–2124 (1991), and Qoronfleh et al., *J. Bacteriol.* 174:7902–7909 (1992).

For essential genes, the *S. flexneri* virB promoter can be used, with *S. flexneri* virF gene and promoter elsewhere on the same plasmid, on a separate plasmid, or on the chromosome (Hromockyi et al. (1992); Tobe et al. (1991). A Yersina two component system for temperature regulation can also be used involving the structural gene for the temperature-regulated positive activator virF (Lambert de Rouvroit et al., *Molec. Microbiol.* 6:395–409 (1992) in combination with promoters of the yopH or yadR genes, with or without modification of the histone-like YmoA protein encoded by ymoA (Cornelis, in *Molecular Biology of Bacterial Infections* (Cambridge University Press, Cambridge, 1992)). The Shigela virF gene is equivalent to lcrF in *Y. pestis* (Hoe et al., *J. Bacteriol.* 174:4275–4286 (1992). Many other repressor-promoter combinations can be adapted to express essential genes in a temperature-specific manner by using temperature-sensitive forms of the repressor. Methods for obtaining temperature-sensitive mutant repressors are well established.

The containment ability of the temperature regulated system can be further augmented by using promoters that function optimally at low temperatures and have minimal activity at 37° C., so that these promoters can be engineered to regulate the expression of the lethal genes or a repressor of the essential genes at low temperatures. Utilization of these promoters provides alternate controls of lethal genes and an additional means to eliminate any residual activity due to low level expression of an essential or replication gene at low temperatures.

Cold-specific expression can also be accomplished by coupling a gene to a cold-shock promoter or a cold-sensitive promoter. Cold shock promoters may be obtained from known cold-shock genes. Cold shock genes with promoters have been described (Jones et al. (1987)). An example of a useful cold-shock promoter is the promoter from cspA (Vasina and Baneyx, *Appl. Environ. Micro.* 62:1444–1447 (1996)). Promoters- with temperature-specific expression can be identified by a promoter probe vector. Such vectors have flanking DNA from a gene that is dispensable and which can readily be selected for or identified using, for example, a chromogenic substrate. Other cold-specific promoters useful for expression of the essential gene can be identified by screening for cold-sensitive lack of expression of β-galactosidase in an *S. typhimurium* lacZ fusion library (Tanabe et al., *J. Bacteriol.* 174:3867–3873 (1992)).

A preferred system that is less complex involves the interaction of the bacteriophage lambda promoters, $\lambda P_L$ and $\lambda P_R$, with the CI857 temperature-sensitive repressor. This system has been described, for example, by Lieb, *J. Mol. Biol.* 16:149–163 (1966). The lambda phage promoters $\lambda P_L$ and $\lambda P_R$, with their mutant temperature-sensitive repressor CI857, provide a tightly regulated system used in expression vectors to provide controlled expression of toxic genes (O'Connor and Timmis, *J. Bacteriol.* 169:4457–4462 (1987)). The cI857 gene product is synthesized but inactive at 37° C. and is synthesized but actively represses expression of genes at 30° C. and below whose transcription is controlled by either $\lambda P_L$ or $\lambda P_R$.

Such a temperature regulated Environmentally Limited Viability System could operate as follows. An expression vector containing the essential *S. typhimurium* asd gene, operatively linked to the bacteriophage lambda promoter left ($\lambda P_L$), and the lethal lysis genes lys13 and lys19 of bacteriophage P22, operatively linked to the bacteriophage P22 promoter right ($P22P_R$), is placed in a bacterial cell having a defined deletion of the *S. typhimurium* asd gene containing an insertion of the bacteriophage P22 c2 repressor gene operatively linked to the bacteriophage lambda promoter right ($\lambda P_R$). The inserted cartridge also contains the temperature-sensitive bacteriophage lambda repressor gene cI857, responsible for the temperature-dependent regulation of $\lambda P_R$ and $\lambda P_L$. This use of lambda promoters allows expression of the gene products encoded by the genes fused to them at temperatures greater than about 30° C., especially at about 37° C., but increasingly represses expression, due to the CI857 repressor, at temperatures below about 30° C. This results in the expression of both the essential asd gene and the bacteriophage P22 C2 repressor at temperatures greater than about 30° C., especially at about 37° C. The bacteriophage P22 C2 repressor in turn prevents the expression of the lethal lysis genes at temperatures greater than about 30° C., especially at about 37° C. The inverse occurs at temperatures below about 30° C., with little or no expression of the asd gene and efficient expression of the P22 lysis genes due to derepression, both of which cause cell lysis and death if the cell attempts growth at temperatures below about 30° C., especially at about 25° C.

This Environmentally Limited Viability System can be reinforced by introducing a temperature-regulated chromosomal polA gene, which is expressed at temperatures greater than about 30° C., especially at about 37° C., but not at temperatures below about 30° C., especially at about 25° C. Since the expression vector containing the asd gene requires expression of the polA gene for replication, the expression vector containing the asd gene will not be able to replicate at temperatures below about 30° C., thus leading to loss of the vector and cell death.

Leaky expression from the control sequences of an Environmentally Limited Viability System, if encountered, can be eliminated in several ways. The level of CI repressor produced can be increased by placing the cI857 gene under the control of a strong constitutive promoter, such as Ptrc, thus providing an excess of the thermosensitive repressor. In addition, more binding sites for the CI repressor can be introduced within the operator region of $\lambda P_R$ to reduce transcriptional starts at non-permissive temperatures, or engineered into regions downstream of the promoter element to hinder transcription at lower temperatures. Additionally, an antisense RNA for the regulated gene could be transcribed from a differently regulated promoter oriented in the opposite direction to $\lambda P_R$.

3. Arabinose Regulation. A preferred regulatory system for triggering the expression switch when a microorganism is moved from a permissive to a non-permissive environment is the araC-$P_{BAD}$ system. The araC-$P_{BAD}$ system is a tightly regulated expression system which has been shown to work as a strong promoter induced by the addition of low levels of arabinose (see Guzman et al., *J. Bacteriol.* 177(14) :4121–4130 (1995)). The araC-araBAD promoter is a bidirectional promoter controlling expression of the araBAD genes in one direction, and the araC gene in the other direction. For convenience, the portion of the araC-araBAD promoter that mediates expression of the araBAD genes, and which is controlled by the araC gene product, is referred to herein as $P_{BAD}$. For use in the vectors and systems described herein, a cassette with the araC gene and the araC-araBAD promoter should be used. This cassette is referred to herein as araC-$P_{BAD}$. The AraC protein is both a positive and negative regulator of $P_{BAD}$. In the presence of arabinose, the AraC protein is a positive regulatory element which allows expression of $P_{BAD}$. In the absence of arabinose, the AraC protein represses expression of $P_{BAD}$. This can lead to a 1,200-fold difference in the level of expression from $P_{BAD}$.

Regulation with arabinose is especially useful for delayed death Environmentally Limited Viability Systems. This is because, once arabinose is no longer supplied, it takes time for the arabinose concentration to decline sufficiently to allow the AraC protein to begin acting as a repressor. To extend the time of temporary viability, it is preferred that strains for use with an arabinose regulated Environmentally Limited Viability System contain a deletion of the araC-araBAD operon. Such a deletion prevents metabolism of arabinose, leading to a higher intracellular level of arabinose. This results in a longer delay before arabinose levels decline sufficiently to allow the AraC protein to begin acting as a repressor. Regulation with arabinose is also useful since free arabinose is not generally available in nature. For example, arabinose is absent from avian tissues. This results in Environmentally Limited Viability Systems in which the only permissive environment is a carefully controlled artificial environment, such as in a fermenter.

Arabinose regulation is most usefully employed with other regulatory elements in an Environmentally Limited Viability System. In the examples describe below, additional regulatory elements are derived from either bacteriophages P22 or lambda or other bacterial regulatory systems, such as the LacI$^q$ repressor of *E. coli*. The lethal genes employed are derived from either bacteriophage lysis genes, bacterial nuclease genes or colicin genes, while the essential genes which could be regulated by this system include the asd, thyA, purA and lpx genes. The incorporation of one or more of these components will then result in a microorganism which can grow well in a fermenter supplied with low levels of arabinose, can colonize a desired host and produce expression products for a limited time, and then commence to die due to the expression of lethal genes, lack of expression of essential genes, or both. Strains containing these systems would then be unable to grow in any environment lacking arabinose, thus preventing their spread in the environment. As another example, arabinose regulation can also be used to control expression of replication genes in an Environmentally Limited Viability System. Thus, for example, polA can be operatively linked to araC-$P_{BAD}$.

Figure 9A:
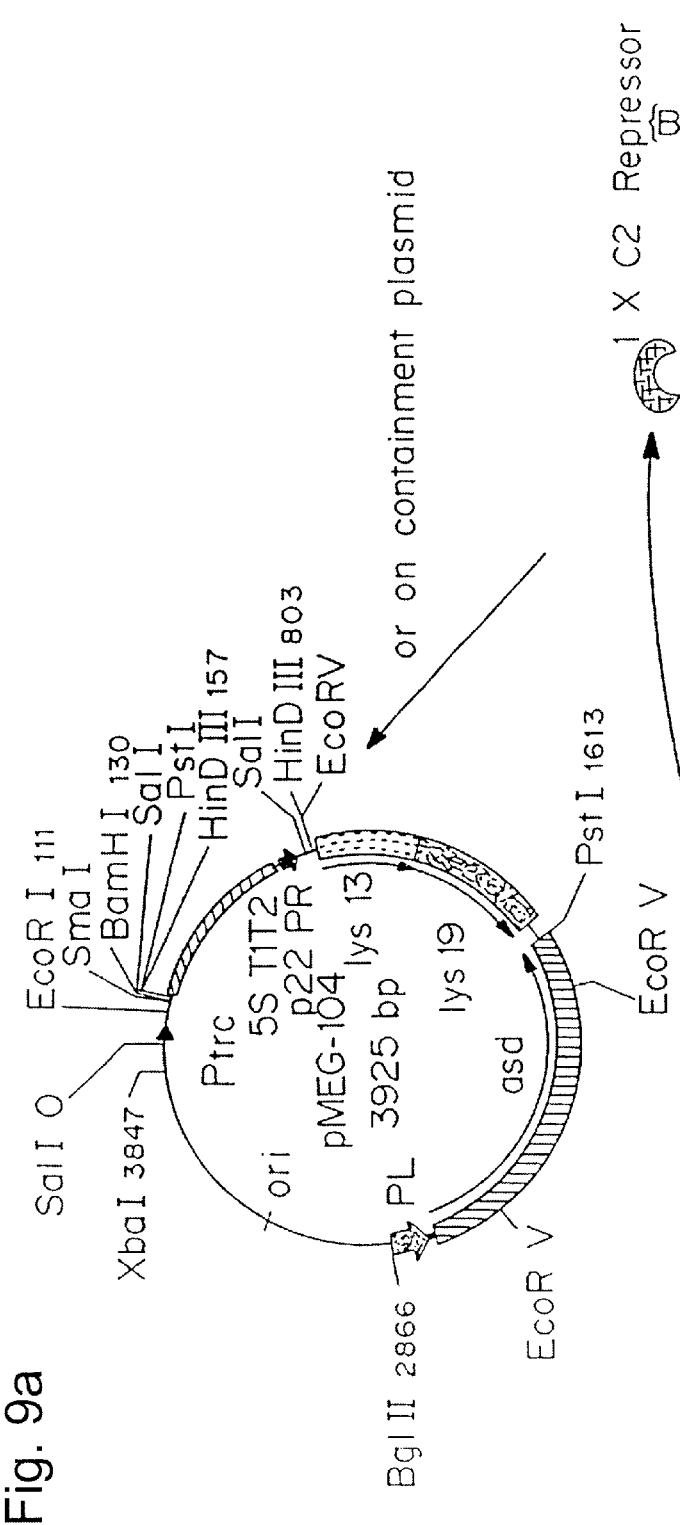
FIGS. 9a and 9b are diagrams of an arabinose regulated Environmentally Limited Viability System. A chromosomally based arabinose regulation system produces the C2 repressor responsible for the repression of either chromosomally or plasmid encoded lysis genes. Growth of the strain in the presence of arabinose would produce a limited amount of C2 repressor which would prevent expression of the lysis genes for a time dependent on the number of repressor targets present in a given strain. The chromosomally based lysis genes should allow the strain to persist longer within the non-permissive environment than the plasmid born lysis system.
Figure 9B:
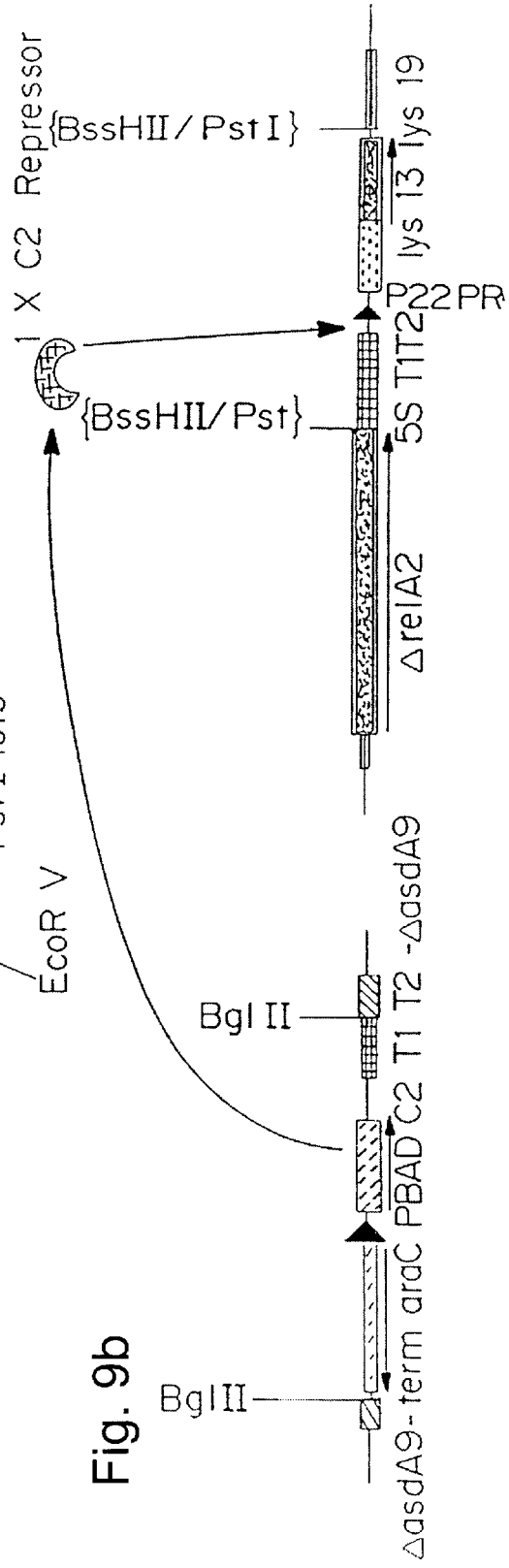
Figures 13A, 13B, 13C:
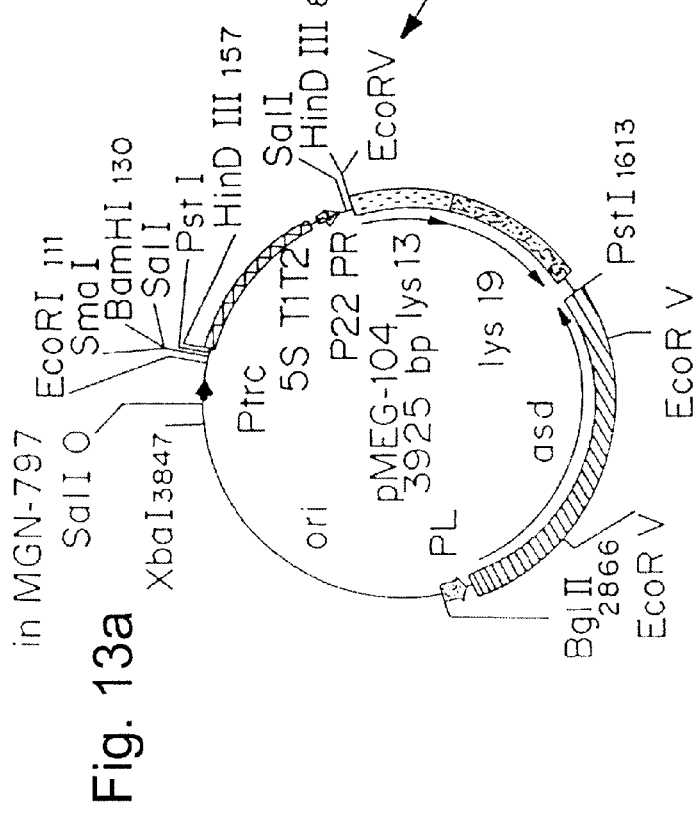
FIGS. 13a, 13b and 13c are diagrams of an arabinose regulated delayed death Environmentally Limited Viability System with a chromosomally encoded C2 repressor. The presence of arabinose results in the production of the C2 repressor which in turn prevents the expression of the lysis genes, shown on the two alternative plasmids pMEG-104 and pMEG-209. pMEG-209 is derived from pMEG-104 and provides the temperature-sensitive CI857 repressor responsible for repressing the asd gene in strains lacking CI repressor. Death of the cells in a non-permissive environment is governed by the C2 repression of the lysis genes, and, in the case of pMEG-209 in strain MGN-798, also prevents asd expression at temperature below 30° C.

Both FIG. 9 and FIG. 13 show lysis based systems where araC-$P_{BAD}$ drives expression of the C2 repressor in the permissive environment containing arabinose. The C2 repressor is required to prevent expression of the P22 lysis genes driven by P22 $P_R$ present on either a multi-copy number plasmid or elsewhere in the chromosome. Introduction of the strain into an environment without arabinose results in a dilution of the C2 repressor present until the lysis products kill the cell. FIG. 10 shows a similar lysis based system where the arabinose regulated c2 repressor gene has been placed on a multi-copy number plasmid. This system should function as that in FIG. 9, but the higher level of C2 repressor provided by the multi-copy number plasmids should allow increased survival time within the host.

Figures 11A, 11B:
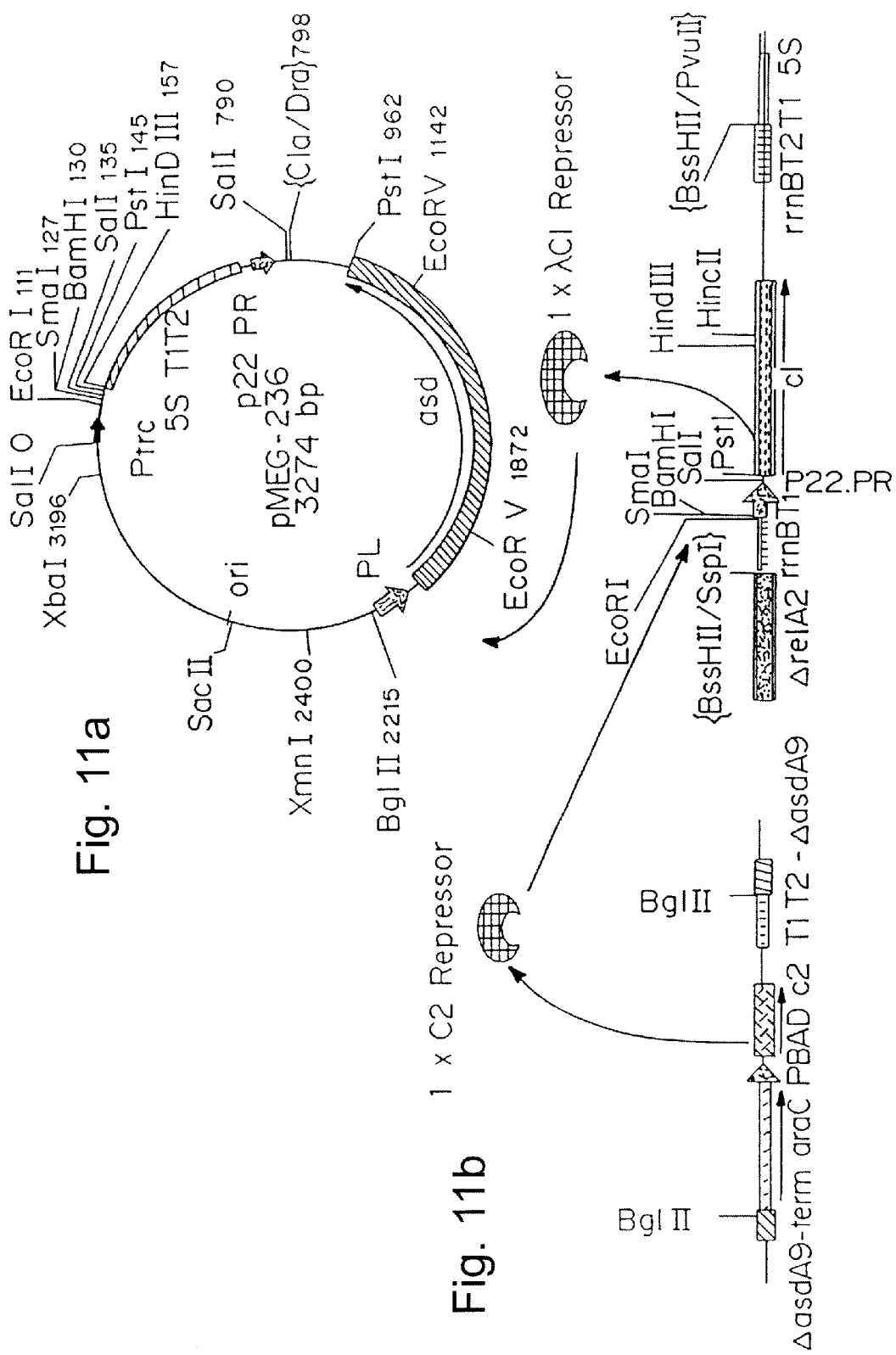
FIGS. 11a and 11b are diagrams of an arabinose regulated delayed death Environmentally Limited Viability System employing a sequential chain of regulators to delay the repression of the essential asd gene in a non-permissive environment. The C2 repressor is produced in the presence of arabinose and prevents the expression of the cI gene. Upon introduction of the strain into an environment lacking arabinose, the C2 repressor is no longer produced and the CI repressor begins to be produced from the chromosome and antisense asd RNA is produced from the plasmid $P_R$. CI then prevents expression of the essential asd gene, eventually resulting in DAPless death of the cell.
Figure 12:
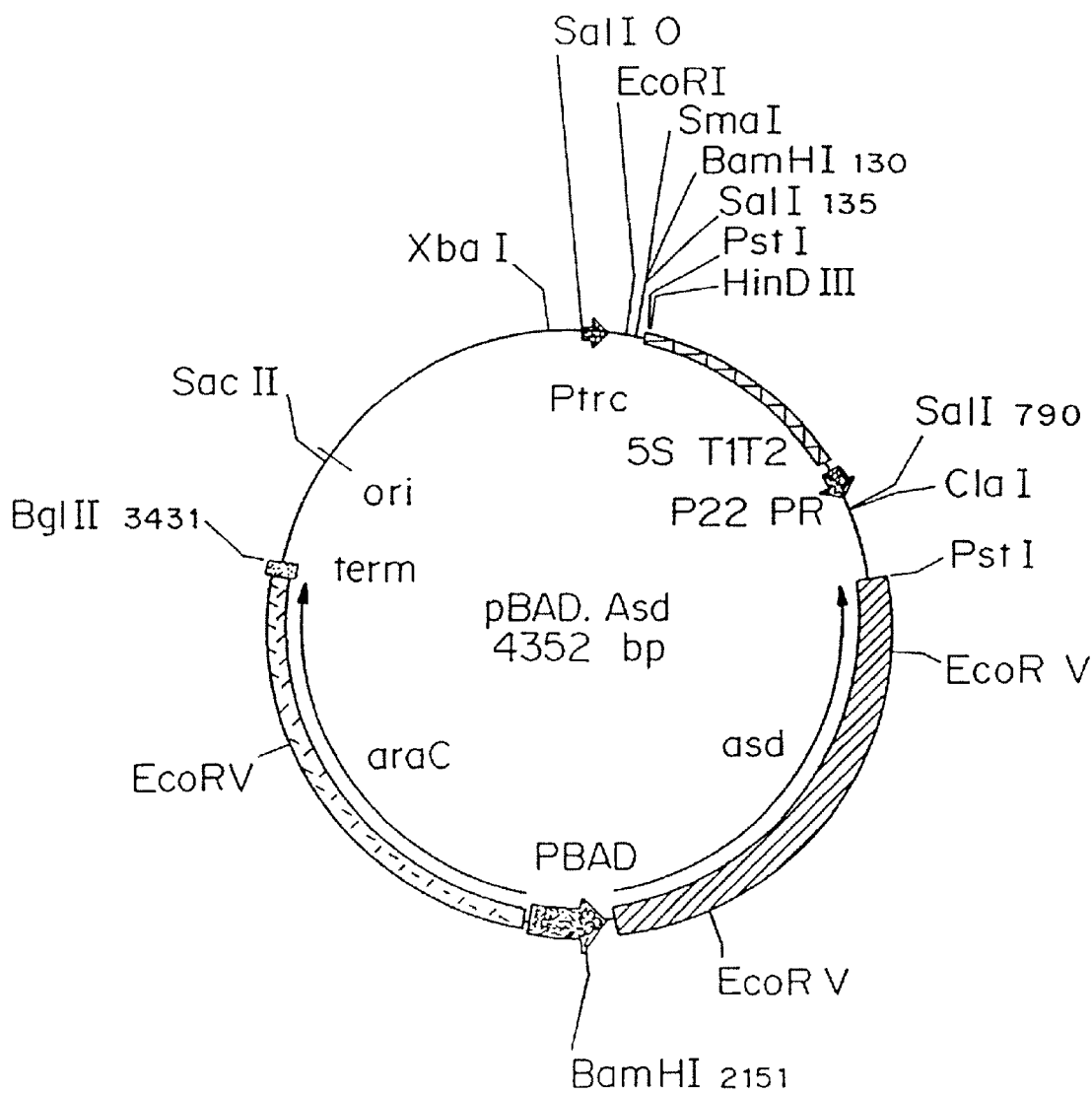
FIG. 12 is a diagram of vector pBAD.Asd. The vector controls the essential asd gene directly with araC-$P_{BAD}$.

FIG. 11 depicts an indirect arabinose regulated essential asd gene. The arabinose promoter in this example drives expression of the C2 repressor which in turn shuts off production of the lambda CI repressor and prevents expression of asd antisense RNA from the P22 $P_R$, thus allowing expression of the asd gene in the fermenter. When the strain enters an environment lacking arabinose, the C2 repressor is no longer produced allowing expression of antisense RNA for asd on the plasmid and lambda CI repressor production as the C2 repressor is diluted. When the CI repressor reaches concentrations high enough to stop Asd production, the cell begins to dilute the intracellular pool of aspartate semialdehyde dehydrogenase and subsequently its pool of DAP, eventually resulting in DAPless death of the cell. In addition, the loss of C2 repressor allows production of antisense asd RNA since P22 $P_R$ on pMEG-236 is no longer repressed. FIG. 12 depicts a system similar to that in FIG. 11 where the asd gene is directly regulated by the arabinose promoter. This system allows growth of the strain in environments containing arabinose as in the system in FIG. 11, but the onset of DAPless death in the non-permissive environment will occur sooner than in the system presented in FIG. 11.

Enteric bacteria contain arabinose regulatory systems homologous to the araC araBAD system from *E. coli*. For example, there is homology at the amino acid sequence level between the *E. coli* and the *S. typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. typhimurium* $P_{BAD}$. Thus, an Environmentally Limited Viability System can employ multiple arabinose regulatory sequences from multiple enterics to differentially regulate different components in the same Environmentally Limited Viability System.

4. Maltose Regulation. Another preferred regulatory system for triggering the expression switch when a microorganism is moved from a permissive to a non-permissive environment is the malT system. malT encodes MalT, a positive regulator of four maltose-responsive promoters ($P_{PQ}$, $P_{EFG}$, $P_{KBM}$, and $P_S$). The combination of malT and a mal promoter creates a tightly regulated expression system which has been shown to work as a strong promoter induced by the addition of maltose (see Schleif, "Two Positively Regulated Systems, ara and mal" in *Escherichia coli and Salmonella Cellular and Molecular Biology* (Neidhardt et al., eds., ASM Press, Washington, D.C., 1996), pages 1300–1309). Unlike the araC-$P_{BAD}$ system, malT is expressed from a promoter ($P_T$) functionally unconnected to the mal promoters. $P_T$ is not regulated by MalT. The malEFG-malKBM promoter is a bidirectional promoter controlling expression of the malKBM gene in one direction, and the malEFG gene in the other direction. For convenience, the portion of the malEFG-malKBM promoter that mediates expression of the malKBM gene, and which is controlled by the malT gene product, is referred to herein as $P_{KBM}$, and the portion of the malEFG-malKBM promoter that mediates expression of the malEFG gene, and which is controlled by the malT gene product, is referred to herein as $P_{EFG}$. Full induction of $P_{KBM}$ requires the presence of the MalT binding sites of $P_{EFG}$. For use in the vectors and systems described herein, a cassette with the malT gene and one of the mal promoters should be used. This cassette is referred to herein as malT-$P_{mal}$. In the presence of maltose, the MalT protein is a positive regulatory element which allows expression of $P_{mal}$.

Regulation with maltose is especially useful for delayed death Environmentally Limited Viability Systems. This is because, once maltose is no longer supplied, it takes time for the maltose concentration to decline sufficiently to abolish induction by the MalT protein. To extend the time of temporary viability, it is preferred that strains for use with an maltose regulated Environmentally Limited Viability System contain a deletion of the one or more elements of the mal operon. Such a deletion prevents metabolism of maltose, leading to a higher intracellular level of maltose. This results in a longer delay before maltose levels decline sufficiently to abolish induction by the MalT protein. Regulation with maltose is also useful since free maltose is not generally available in nature. This results in Environmentally Limited Viability Systems in which the only permissive environment is a carefully controlled artificial environment, such as in a fermenter.

Maltose regulation is most usefully employed with other regulatory elements in an Environmentally Limited Viability System. In the examples describe below, additional regulatory elements are derived from either bacteriophage P22, lambda or other bacterial regulatory systems, such as the LacI$^q$ repressor of E. coli. The lethal genes employed are derived from either bacteriophage lysis genes, bacterial nuclease genes or colicin genes, while the essential genes which could be regulated by this system include the asd, thyA, purA and lpx genes. The incorporation of one or more of these components will then result in a microorganism which can grow well in a fermenter supplied with low levels of maltose, can colonize a desired host and produce expression products for a limited time, and then commence to die due to the expression of lethal genes, lack of expression of essential genes, or both. Strains containing these systems would then be unable to grow in any environment lacking maltose, thus preventing their spread in the environment. As another example, maltose regulation can also be used to control expression of replication genes in an Environmentally Limited Viability System. Thus, for example, polA can be operatively linked to malT. Enteric bacteria contain maltose regulatory systems homologous to the mal operon system from E. coli.

E. Delayed Death

As an alternative to rapid cell death in a non-permissive environment, the Environmentally Limited Viability System can be designed to allow the host microorganism to remain viable for a limited time in a non-permissive environment. This can be referred to as a delayed death Environmentally Limited Viability System and results in temporarily viable microorganisms. In a delayed death ELVS, any essential gene of the ELVS is temporarily expressed in the non-permissive environment, and expression of any lethal gene is temporarily delayed when the host microorganism enters a non-permissive environment. A preferred mechanism for delaying death of the ELVS microorganism is to base regulation on a trans regulatory element which must be degraded or diluted before the ELVS can switch to the non-permissive expression regime. In such a system, upon moving the host microorganism from a permissive to a non-permissive environment, a trans regulatory element which maintains the permissive expression regime ceases to be produced. However, as long as the trans regulatory elements already on hand remain in sufficient quantity, the permissive expression regime can remain in effect. Depending on the turnover of the trans regulatory element and the relationship between the amount of trans regulatory element on hand and the amount of trans regulatory element needed to maintain the permissive expression regime, the permissive expression regime can be maintained for several generations after transfer to the non-permissive environment. Such temporary viability can be useful for allowing the host microorganism to deliver an expression product, such as an antigen, to a non-permissive environment, such as an animal, but not remain indefinitely. Preferred trans regulatory elements for use in a delayed death Environmentally Limited Viability System are the AraC protein and arabinose, its inducer. The AraC protein will continue to stimulate expression of any gene operatively linked to $P_{BAD}$ until the concentration of arabinose falls below a critical level.

A delayed death Environmentally Limited Viability System can also be based on the gradual loss of the product of an essential gene after the shift to a non-permissive environment. For example, Asd enzyme activity would remain for a period of time after the switch to the non-permissive environment, until it was degraded and diluted sufficiently to prevent proper cell wall synthesis. For such a system, it is preferred that the essential gene be present on a high copy number plasmid. This allows for the longest delay by producing a large amount of the essential gene product prior to the switch to the non-permissive environment. A preferred type of delayed death Environmentally Limited Viability System would have $P_{BAD}$ operatively linked to the Salmonella typhimurium asd gene, so that the expression of the asd gene would be dependent on the presence of arabinose. Depending on the copy number of the vector containing the araC-$P_{BAD}$ asd fusion, the onset of DAPless death would vary dependent on the time needed to dilute the stable Asd enzyme sufficiently to preclude adequate synthesis of DAP for cell wall stability. Thus, the number of viable cell divisions for the ELVS microorganism in the animal can be modulated prior to the onset of DAPless death and lysis.

It is preferred that, in a delayed death Environmentally Limited Viability System, the genes encoding the trans regulatory elements be placed on multicopy vectors and that the lethal genes be located on the chromosome. This allows for a greater delay by increasing the amount of trans regulatory element present relative to the promoters (or other elements) controlled by the trans regulatory element. Such balancing between the amount of trans regulatory factor present and the number of elements to be controlled can be used to adjust the period of time that the onset of cell death is delayed. For example, placing the lethal genes on a multicopy plasmid and/or placing the gene encoding the trans regulatory element on the chromosome would each reduce the delay. Generally, longer delays are preferred since the primary purpose of the disclosed Environmentally Limited Viability Systems is to prevent unlimited growth in non-permissive environments.

The use of the arabinose promoter in a delayed Environmentally Limited Viability Systems has been demonstrated using pMEG-104 and strain MGN-797 (see FIG. 13). The lambda P22 C2 repressor is expressed from the chromosome of MGN-797 under the control of araC-$P_{BAD}$. In MGN-797, the P22 c2 gene is inserted into the chromosomal copy of the asd gene, thus creating a need for the asd gene carried on pMEG-104. On pMEG-104, the lethal lysis genes lys13 lys19 are under the control of P22 $P_R$ which is controlled by the P22 C2 repressor. In the presence of arabinose, C2 repressor is produced from the chromosomal c2 gene. The C2 repressor prevents expression of the lethal lysis genes. In the absence of arabinose, the C2 repressor is no longer produced. When the concentration of the C2 repressor falls, the lethal lysis genes are no longer repressed and the cell lyses.

Figure 14:
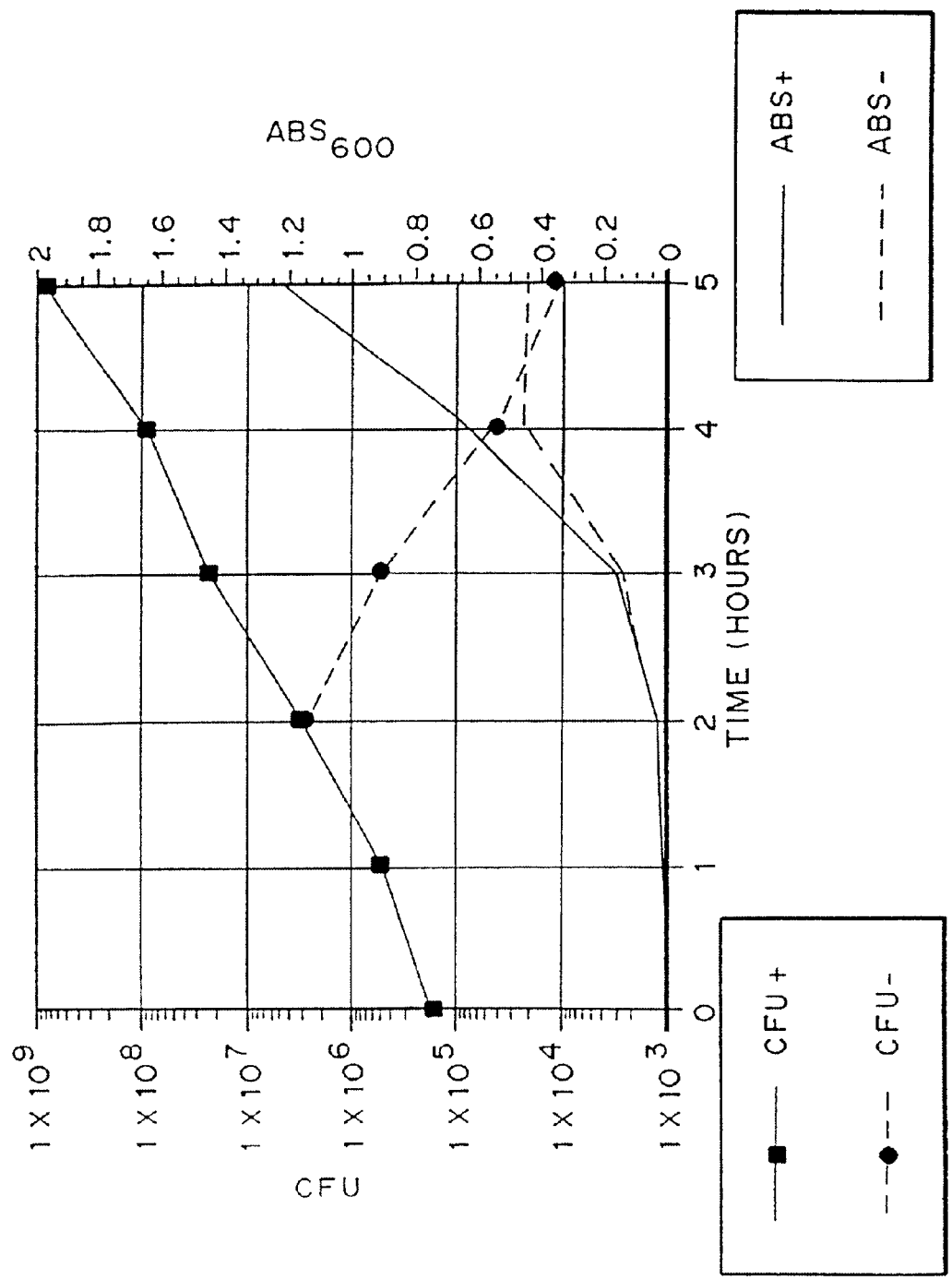
FIG. 14 is a graph showing growth of an arabinose regulated delayed death Environmentally Limited Viability System in terms of colony forming units and absorbance, both versus time of incubation. Growth patterns following transfer of cells grown in the presence of 0.2% arabinose to media either lacking or containing 0.2% arabinose are displayed. The dark solid lines represent the growth with arabinose, while the light dashed lines represent the growth without arabinose. The lines with either square or circular points indicate the total colony forming units observed over time, while the lines without squares or circles represent the absorbance of the culture at a given time. Both the colony forming units recovered and the absorbance observed during growth without arabinose demonstrate the temporary viability of the Environmentally Limited Viability System in the non-permissive environment.

FIG. 14 shows the effect of this Environmentally Limited Viability System on the cells in the presence and absence of arabinose. MGN-797 harboring pMEG-104 was grown in the presence of arabinose and then transferred into media with or without arabinose (time zero on the graph). The graph reveals the onset of lysis induced cell death within 2 hours or approximately 4 generations following introduction into media without arabinose. Thus, this system is effectively a delayed death Environmentally Limited Viability System.

It is preferred that for delayed death Environmentally Limited Viability Systems administered to animals, both the animal and the natural environment outside of the animal are non-permissive environments. In such cases, it is preferred that the only permissive environment be those of controlled growth, such as in a fermenter, where growth and/or survival of the microorganism is dependent on conditions which can be created artificially but which do not generally exist in nature.

E. Vectors

The disclosed Environmentally Limited Viability System will employ, unless otherwise indicated, conventional techniques of cell culture, molecular biology, microbiology, and recombinant DNA, which are within the skill of the art. Such techniques are explained fully in the literature. See, for example, Sambrook et al., *Molecular Cloning: A Laboratory Manual* (1989); *DNA Cloning*, Volumes I and II (Glover, ed., 1985); *Oligonucleotide Synthesis* (Gait ed., 1984); *Nucleic Acid Hybridization* (Hames and Higgins, eds., 1984); Perbal, *A Practical Guide To Molecular Cloning* (1984); the series, *Methods in Enzymology* (Academic Press, Inc.); *Vectors: A Survey Of Molecular Cloning Vectors And Their Uses* (Rodrigues and Denhardt, eds., Butterworths, 1987); Miller, *Experiments In Molecular Genetics* (Cold Spring Harbor Laboratory, 1972); and Miller, *A Short Course In Bacterial Genetics* (Cold Spring Harbor Laboratory, 1992).

As used herein, "vector" refers to an autonomously replicating nucleic acid unit. Many types of vectors are known with the most common and useful types being plasmid vectors, viral vectors, cosmid vectors, and phasmid vectors.

A diversity of vectors possessing different promoters, multiple cloning sequences, and different plasmid replicons can be used, so that the amount of a synthesized foreign antigen can be controlled by the relative number of gene copies. For example, vectors with p15A, pBR and pUC replicons can be constructed, all of which are dependent on the polA gene encoding DNA polymerase I for their replication. Determination of whether replication of a vector is dependent on DNA polymerase I can be accomplished by growing the vector in a host with a temperature-sensitive polA mutation, such as χ1891 (see Table 1), and checking for vector maintenance as a function of temperature. Preferably, vectors used in the Environmentally Limited Viability System do not use antibiotic resistance to select for maintenance of the vector.

Figure 3:
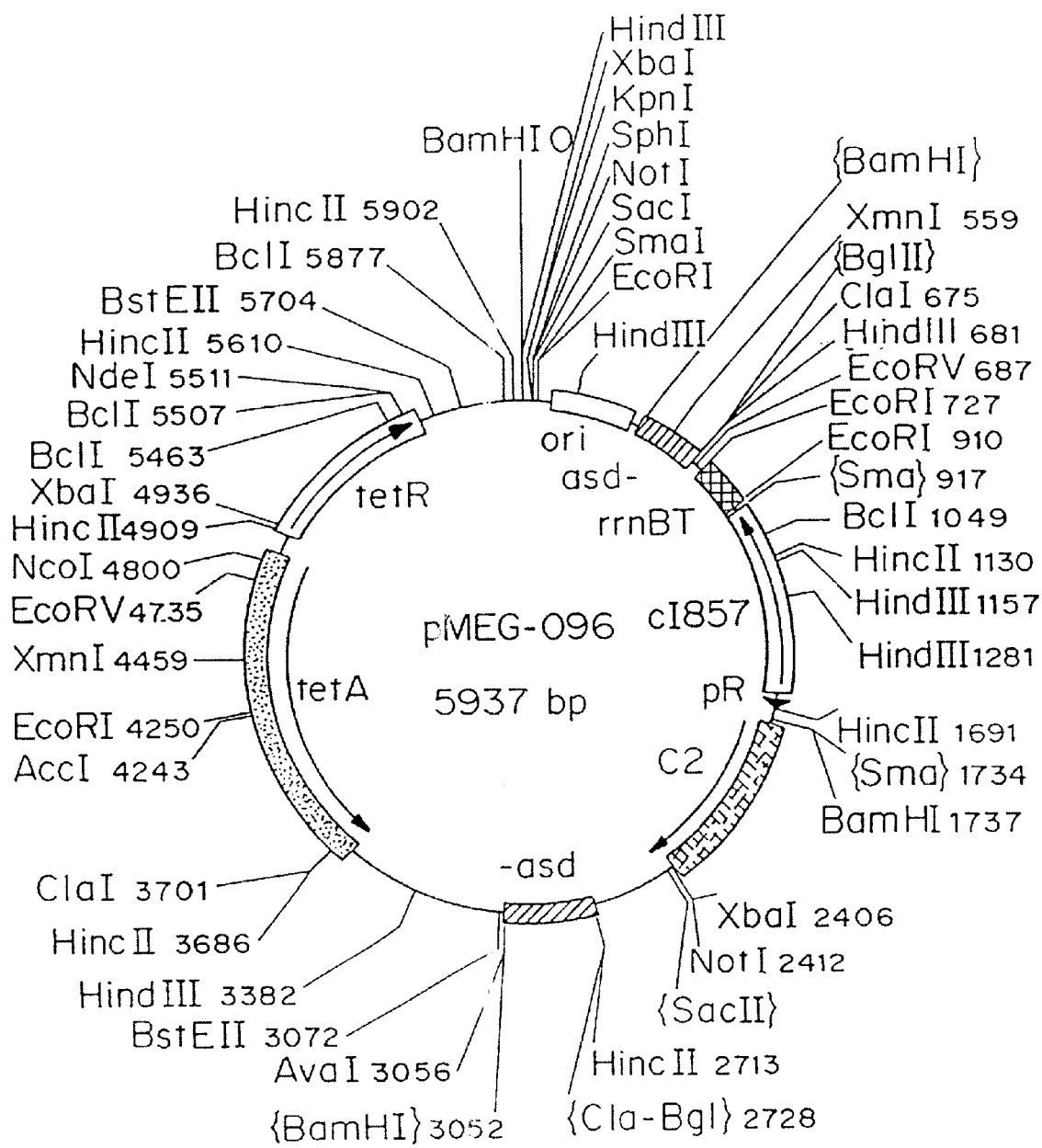
FIG. 3 is a diagram of the pir-dependent suicide vector pMEG-096 containing the bacteriophage P22 c2 repressor gene (C2) operatively linked to the bacteriophage lambda promoter right ($P_R$) and the bacteriophage lambda temperature-sensitive repressor cI857 gene, both genes in a cartridge flanked by portions of the *S. typhimurium* asd gene (hatched with diagonal lines). This arrangement allows allele replacement of the wild-type chromosomal asd gene of any strain with homology to the flanking asd gene segments.
Figures 4A, 4B:
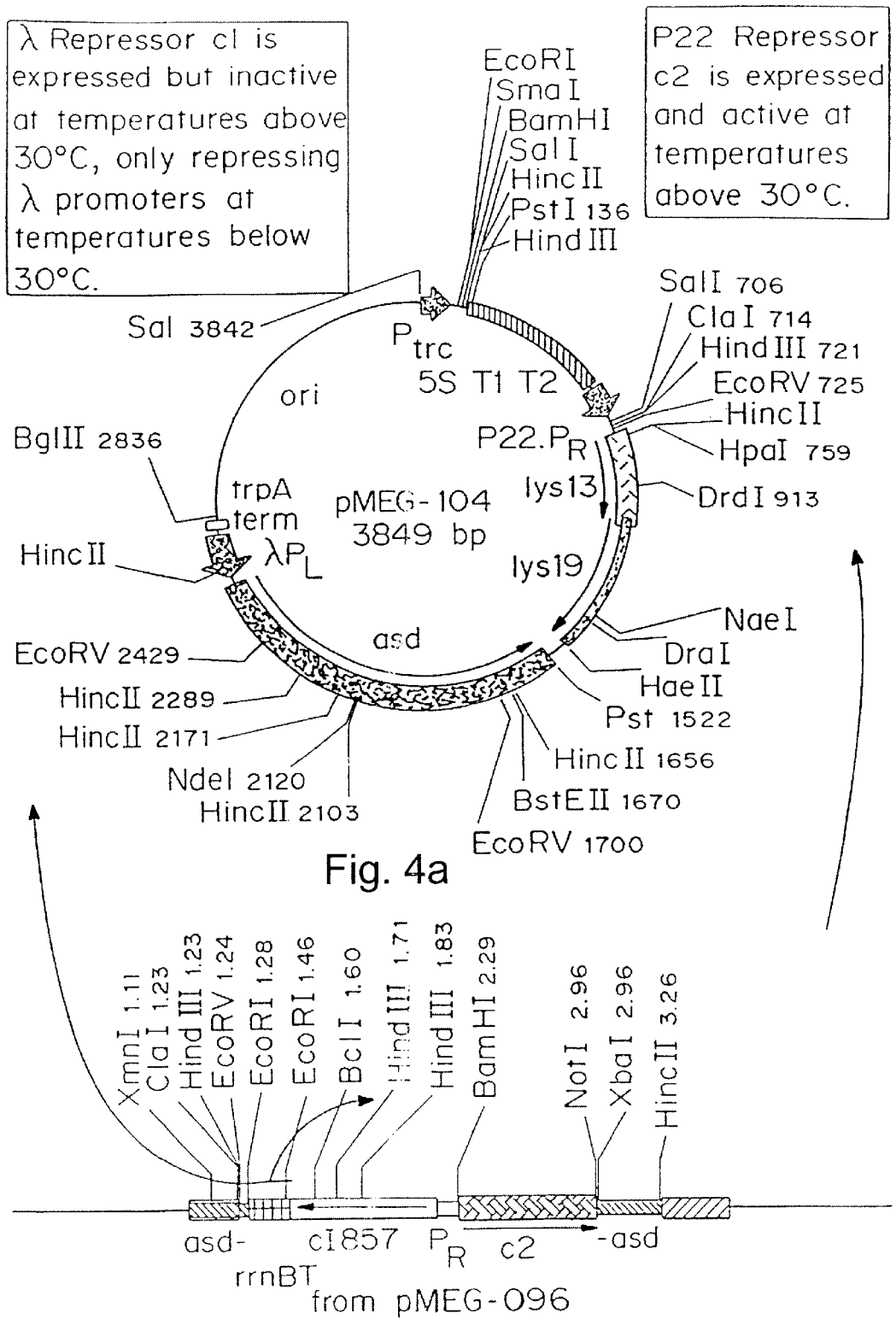
FIGS. 4a and 4b are diagrams of a vector based Environmentally Limited Viability System (ELVS) with *S. typhimurium* host MGN-392 containing expression vector pMEG-104, the combination designated as strain MGN-417. pMEG-104 contains the asd gene of *S. typhimurium* operatively linked to the promoter. left of bacteriophage lambda ($\lambda P_L$), and the lysis genes of bacteriophage P22 (lys13 and lys19) operatively linked to the promoter right of bacteriophage P22 ($P22.P_R$). The promoter left of bacteriophage lambda and promoter right of bacteriophage P22 are placed in opposite orientations on the vector such that transcription of the promoter left of bacteriophage lambda will produce an antisense RNA of the lysis genes and transcription of the promoter right of bacteriophage P22 will produce an antisense RNA of the asd gene. Both genes are in a cartridge flanked by two different transcription terminators (trpA term and 5S T1 T2). pMEG-104 also contains the low copy-number, DNA polymerase I-dependent p15A origin of replication (ori). The host cell MGN-392 contains the cI857 and c2 repressor gene cartridge derived from pMEG-096 on its chromosome. This cartridge replaces a central portion of the chromosomal asd gene of the host cell. This cartridge provides thermally regulated limited viability when the plasmid pMEG-104 is present in this host cell. Bold arrows depict temperature-regulated expression of the vector components of the ELVS.

A preferred vector, pMEG-104, including both an essential gene and lethal gene is shown in FIG. 4. This vector is suitable for the expression of various foreign antigens in a recombinant avirulent Salmonella, and in other enteric bacteria modified by introduction of a defined asd deletion containing the repressor elements by using the suicide vector pMEG-096 (FIG. 3). Genes for such antigens can be cloned into the multiple cloning site and expressed under the control of the constitutive Ptrc. The host strain has the λcI857 gene chromosomally located and constitutively expressed under the control of the native promoter ($P_{RM}$) The λcI857 gene product is inactive at 37° C. and will not repress the $\lambda P_L$ which is driving the expression of the chromosomal P22 c2 wild-type gene (the c2 gene in P22 is equivalent to the cI gene in lambda). The expression of the P22 c2 gene at 37° C. will repress the $P22P_R$ and thus preclude expression of the plasmid-encoded lysis genes 13 and 19. The asd gene in the plasmid vector will be expressed, however, since the λcI857 protein is inactive at 37° C. and the asd gene will be expressed under the control of $\lambda P_L$. At 30° C. or lower, the λCI857 protein exhibits a wild-type phenotype. It will repress the expression of the P22 c2 gene, which will therefore result in an insufficient quantity of c2 repressor and the lysis genes lys13 and lys19 will be expressed because of transcription initiated at the $P22P_R$. On the other hand, the functional λcI857 gene product will now repress $\lambda P_L$ leading to cessation of synthesis of the asd gene product. It should be noted that the asd genes and the lysis genes lys13 and lys19 are arranged with no transcription terminations between them such that at 30° C. and below, the mRNA for the lysis genes lys13 and lys19 will extend into the asd gene but with an incorrect orientation and thus constitute an antisense RNA that will further eliminate expression of the asd gene. Just the opposite occurs at 37° C. such that the asd gene message will extend into the lysis genes 13 and 19 and serve as an antisense RNA to completely shut down the expression of the lysis genes. It should be noted that if the plasmid is transferred to another microorganism, the lysis genes will be expressed constitutively and lead to the demise of the recipient cell. Thus the containment host-vector system prevents both survival and spread of the microbial strain within the environment and transmission of recombinant plasmids within natural populations of bacteria.

Transfer Vectors. Rather than expressing an expression product directly, a microorganism containing an Environmentally Limited Viability System can harbor a vector for transfer to, and expression in, another cell in the environment into which the microorganism is placed. As used herein, a transfer vector is an expression vector which can be transferred from a microorganism with an Environmentally Limited Viability System into a cell, and which directs the expression of an expression gene encoded by the transfer vector. It is intended that the transfer vector can contain any expression gene, including genes encoding antigens, immunomodulators, enzymes, and expression products which regulate gene expression or cellular activity in the recipient cell.

Preferred recipients for transfer vectors are cells of animal hosts. For this purpose, microorganisms containing an Environmentally Limited Viability System and a transfer vector can be administered to an animal host. It is preferred that the microorganism invade host cells in order to deliver the transfer vector. For this purpose, it is preferred that the Environmentally Limited Viability System cause lysis of the microorganism once it enters a cell of the host animal. This will release the transfer vector inside the recipient cell. For expression of genes on the transfer vector in recipient cells, it is preferred that the expression genes be operatively linked to expression control sequences operable in the recipient cell. For example, where the recipient cell is an animal cell, it is preferred that the expression genes be operatively linked to a promoter functional in the animal.

Transfer vectors may also contain replication sequences operable in the recipient cell. This would allow replication of the transfer vector, resulting in increased or longer expression of expression genes present on the transfer vector. Transfer vectors are especially useful for expression of antigens and other proteins that need to be glycosylated or post-translationally modified in a eukaryotic cell. In this way a bacterial cell with an Environmentally Limited Viability System can be used for delivery of a protein requiring eukaryotic processing by expressing the protein from a transfer vector.

An example of a vector suitable for use as a transfer vector in a microorganism with an Environmentally Limited Viability System is described by Sizemore et al., Science 270:299–302 (1995). Sizemore et al. used a construct expressing β-galactosidase under the control of the immediate early cytomegalovirus promoter and observed the expression of β-galactosidase in eucaryotic cells following lysis of a Δasd Shigella strain due to DAPless death.

A preferred use for transfer vectors is in a live bacterial antigen delivery system for stimulation of an immune response in a host animal. For this purpose it is preferred that the bacteria is avirulent Salmonella, Shigella, Yersinia, or invasive Escherichia that would invade and then lyse to liberate a transfer vector designed for expression in cells of the animal host. This can be useful in stimulating an immune response for viruses, parasites or against gamete antigens where the antigens are normally glycosylated or post translationally modified in some way that can only be accomplished when the antigen product is synthesized within the eucaryotic cell.

The efficiency of transfer of a transfer vector can be improved by including an endA mutation, mutations in recBC (with or without sbc suppressor mutations), and/or mutations in other nuclease genes. Such mutations can reduce degradation of the transfer vector upon lysis of the bacterial cell. It is also possible to influence the host cell type and the mucosal surface to which the microorganism containing the transfer vector would adhere to and invade. This can be achieved by blocking or turning on the expression of specific adhesins and/or invasins.

Figure 7:
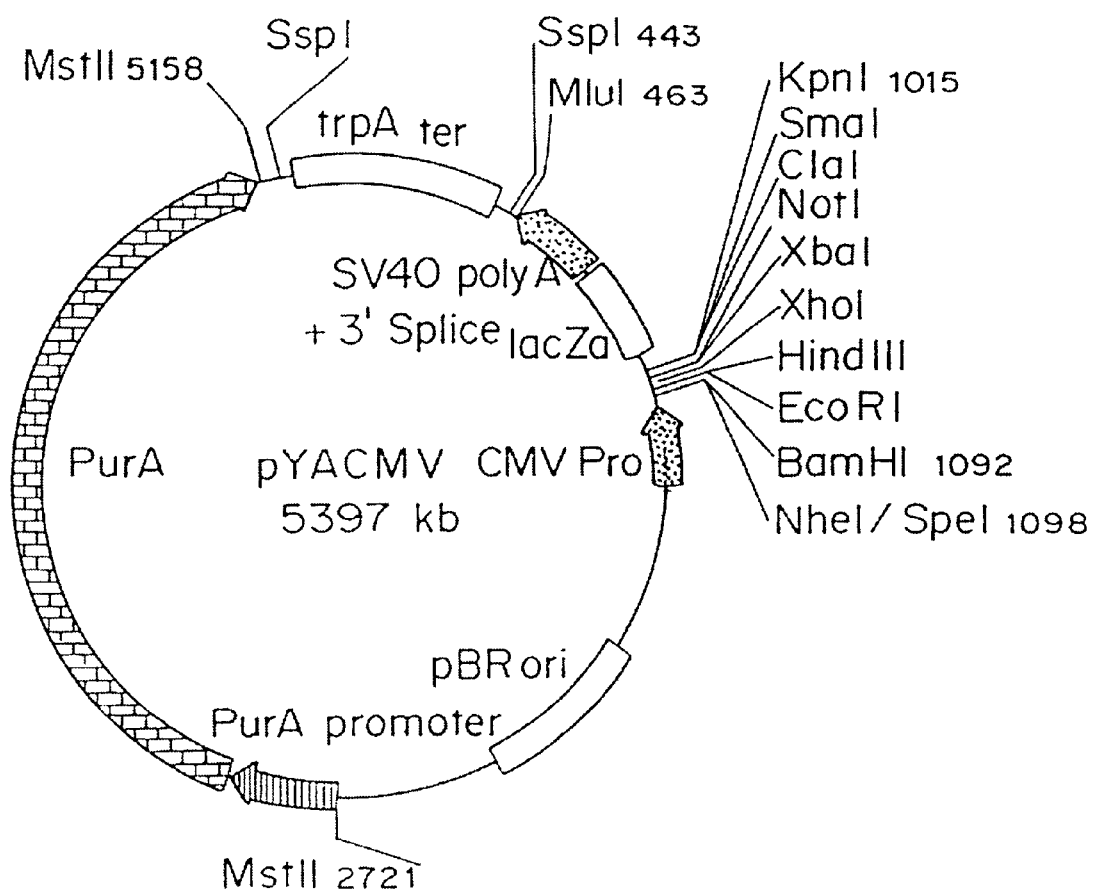
FIG. 7 is a diagram of transfer vector pYACMV. The vector contains the purA gene as a selective marker (used in a $\Delta$purA strain), a pBR322 replicon for high levels of plasmid within the delivery system, and eukaryotic expression elements including the CMV intermediate early promoter/enhancer (MacGregor and Caskey, *Nuc. Acids Res.* 17:2365 (1989)) and the SV40 polyA and splice elements for effective expression of the cloned antigen within the eukaryotic host.

Many vectors are known for DNA immunization or introduction into cells in an animal. Such vectors can be used as transfer vectors in microorganisms containing an Environmentally Limited Viability System. In this case, the Environmentally Limited Viability System provides a useful means for introducing such vectors into cells. Preferred promoters for expression of expression genes on transfer vectors are adenovirus, herpes virus and cytomegalovirus promoters. Expression of the expression gene can also be increased by placing a bacterial promoter upstream of the eucaryotic promoter, so that the bacterial strain would already express some of the expression product. This expression product would be liberated upon lysis of the bacterium. An example of a transfer vector is shown in FIG. 7. This vector makes use of PurA$^+$ as a selectable marker for use in a ΔpurA mutant strain. This constitutes another type of balanced-lethal host-vector system since purA mutants are unable to grow in animal tissues. The transfer vector can also be designed to exhibit runaway replication following entry of the bacterial cell into a eucaryotic cell. An example of this is included in the Environmentally Limited Viability System depicted in FIG. 8.

Preferred bacterial hosts/strains and vectors useful in, or useful for constructing, Environmentally Limited Viability Systems are listed in Tables 1, 2, and 3.

TABLE 1

Strains and Plasmids Useful in the Construction and Confirmation of Environmentally Limited Viability Systems

| Strain | Description | Genotype |
|---|---|---|
| $\chi$1891 | E. coli K-12 temperature-sensitive polA mutant | F-thr txs purE supE42 λ-ΔtrpE his gryrA srl thyA57 T3$^r$ mtiA polA12$_{(ts)}$ cycA cycB |
| $\chi$3730 | S. typhimurium LT-2 Asd$^-$ intermediate host strain that is reversibly rough and has three of the S. typhimurium host restriction systems inactivated | leu hsdLT galE trpD2 tpsL120 ΔasdA1 Δ[zhf-4:Tn10] metE551 metA22 hsd5A hsdSB ilv |
| $\chi$3761 | S. typhimurium UK-1 virulent wild-type strain obtained as a chicken passaged spleen isolate. | wild-type |
| MGN-026 | E. coli K-12 DH5α lysogenized with λpir from $\chi$6151. This strain provides lacZα complementation and the ability to support pir-dependent replicons. This strain also transforms well, is an endonuclease mutant, and is recombination deficient, making it useful for recombinant work with the pGP704 derived suicide vectors. | endA1hsdR17 (rk–, mk+) supE44 thi-1 recA1 gyrA relA1 Δ(lacZYA-argF) U169 λpir deoR (φ80dlacΔ(lacZ)M15) |
| MGN-336 | E. coli strain for the P22 lysis vectors obtained by electroporating $\chi$6097 with pMEG-096 to provide a single integration of the c2 repressor genes in the asd gene. This provides the λP$_R$ driven P22 c2 gene and lambda cI857 between either part of the S. typhimurium asd deletion inserted into the chromosome, duplicating part of the asd gene of E. coli with that of S. typhimurium. | ara Δ(lac-pro) rpsL ΔasdA4 Δ[zhf-2::Tn10] Δasd-17::cI857PRc2 thi φ80dlacZΔM15 |
| MGN-377 | S. typhimurium UK-1 intermediate ELVS host strain obtained by electroporating $\chi$3761 with large amounts of pMEG-096 (FIG. 3) to obtain a single integration of this cI857PR c2 clone in the asd gene. This provides the λP$_R$ driven P22 c2 gene and λcI857 between either part of the S. typhimurium asd deletion duplicating portions of the wild-type asd gene in the chromosome. | wild-type + integrated pMEG-096 |
| MGN-391 | S. typhimurium UK-1 ELVS host obtained from MGN-377 by selecting for fusaric acid resistant, tetracycline sensitive, Asd$^-$ isolates produced by excision of pMEG096 in MGN-377 leaving the cI857PRc2 cartridge in the defined asd deletion. Sibling of MGN-392 (Table 3). | Δasd-17::cI857PRc2 |

TABLE 1-continued

Strains and Plasmids Useful in the Construction and Confirmation of Environmentally Limited Viability Systems

| Strain | Description | Genotype |
|---|---|---|
| MGN-399 (pMEG-100 + pYA232) | S. typhimurium UK-1 ELVS host MGN-392 containing the intermediate ELVS vector pMEG-100 (FIG. 5), and the lacI$^q$ repressor plasmid pYA232 (Table 2). Obtained by electroporating MGN-392 with pMEG-100 and pYA232. Does not grow at temperatures below 30°C. | (pMEG-100 + pYA232) Δasd-17::cI857PRc2 |
| MGN-401 (pYA292) | S. typhimurium UK-1 ELVS host MGN-392 electroporated with the Asd$^+$ vector pYA292 to provide a positive control for growth of this strain at different temperatures without DAP. | (pYA292) Δasd-17::cI857PRc2 |
| MGN-409 | E. coli K-12 strain MGN-336 electroporated with ELVS vector pMEG-104 (FIG. 4) This construct does not grow at temperatures below 30° C. | ara Δ(lac-pro) rpsL ΔasdA4 Δ[zhf-2::Tn10] Δasd-17::cI857PRc2 thi φ80dlacZDM15 |
| MGN-792 | E. coli K-12 strain used for production of the suicide plasmid pMEG-221, which contains the P$_{BAD}$ regulated c2 gene within the asd-17 deletion, now designated Δasd-19. | endA1 hsdR17 (rk–, mk+) supE44 thi-1 recA1 gyrA relA1 Δ(lacZYA-argF) U169 λpir deoR (φ80dlac Δ(lacZ)M15) |
| MGN-795 | S. typhimurium ELVS parent strain with asd deletion containing the c2 gene regulated by P$_{BAD}$. | Δasd-19 (is Δasd-17::P$_{BAD}$.C2) |
| MGN-797 | S. typhimurium ELVS strain derived from MGN-795, now containing the ELVS plasmid pMEG-104 with the P22 lysis genes regulated by the chromosomally located c2 gene regulated by P$_{BAD}$. | Δasd-19 (is Δasd-17::P$_{BAD}$.C2) |
| MGN-798 | S. typhimurium ELVS strain derived from MGN-795, now containing the ELVS plasmid pMEG-209 with the P22 lysis genes regulated by the chromosomally located c2 gene regulated by P$_{BAD}$, while the asd gene is regulated by the temperature-sensitive cI857 gene product. | Δasd-19 (is Δasd-17::P$_{BAD}$.C2) |

TABLE 2

Plasmids Useful in the Construction and Confirmation of Environmentally Limited Viability Systems

| Plasmid | Description |
|---|---|
| pMEG-011 | A pir-dependent suicide vector with lacZα multiple cloning site derived from pGP704. |
| pMEG-072 | The promoter right of P22HTint, PCR amplified and cloned as a 125 bp BamHI-SalI fragment into the BamHI-SalI sites of pKK232-8 |
| pMEG-076 | The promoter left of lambda PCR amplified from the lambda lysogen $_\chi$2869 and cloned as a 163 bp fragment into the SmaI-BamHI sites of pKK232-8 |
| pMEG-078 | The P22HTint lysis genes lys13 and lys19 PCR amplified as a 797 bp fragment with a SD site at a 5' blunt end and a PstI site designed into the 3' end, cloned into the EcoRV-PstI sites of the low copy vector pWKS30 |
| pMEG-086 | An Asd$^+$ clone obtained by inserting the 314 to 1421 bp asd PCR product lacking the promoter and SD regions as a 1115 bp BglII-blunt fragment, into the BamHI-PvuII sites of pMEG-076. This places asd under the regulation of λP$_L$ |
| pMEG-088 | A PCR clone of the P22 c2 gene driven by λP$_R$ and controlled by the λcI857 gene product. |
| pMEG-089 | The 1060 bp SalI-PvuII fragment of pMEG-078 containing the P22 lysis genes lys13 and lys19 driven by the P22 promoter right cloned into the SalI-PvuII sites of pMEG-072. This construct is toxic unless in a strain expressing P22 c2 repressor |
| pMEG-090 | Intermediate expression vector obtained by BglII partial digestion of pYA810, isolating the 1.6 kb fragment containing the p15A origin of replication, Ptrc, multiple cloning site and 5ST1T2, and ligating to the 1.3 kb BamHI Km$^r$ cartridge of pUC-4K |
| pMEG-096 | The ~2.05 kb ClaI fragment of pMEG-088 ligated into the BglII site of pMEG-006 following treatment with T4 DNA polymerase. This provides the λP$_R$ driven P22 c2 gene and cI857 between either part of the S. typhimurium asd deletion allowing for chromosomal insertion. |
| pMEG-097 | The 1277 bp EcoRI-XbaI fragment of pMEG-86 containing the λP$_L$asd gene cloned into the PvuII-XbaI sites of pMEG-89 using the trpA terminator linker with an internal BglII site and an EcoRI end. This construct is lethal if not in a host with a P22 c2 repressor. |
| pMEG-098 | Derived from pMEG-097 by removing the 28 bp PstI-XbaI fragment of pMEG-097 treating with T4 DNA polymerase, and religating. |
| pMEG-100 | ELVS expression vector intermediate obtained by ligating the 2.26 kb BamHI-BglII fragment of pMEG-098 containing the asdlysis cartridge into the BglII site of pMEG-090. |
| pMEG-104 | ELVS p15A expression vector obtained by deleting the 1.36 kb SalI fragment of pMEG-100 containing the Km$^r$ cartridge. Requires host with P22 C2 repressor. |
| pMEG-236 | ELVS plasmid with λP$_L$ regulated asd, derived from pMEG-104 by deletion of P22 lysis genes. |
| pMEG-209 | ELVS plasmid derived from pMEG-104 by deleting the λPL using restriction enzymes BglII and NdeI, and replacing it with the λcI857P$_R$ BamHI to NdeI fragment of pMEG-014, providing both the λcI regulated promoter right and the thermosensitive CI857 repressor at high levels. |
| pMEG-221 | Suicide donor plasmid derived from pMEG-011 for introduction of Δasd-19 into the chromosome. The asd-19 deletion provides the c2 gene regulated by araC-P$_{BAD}$ flanked by portions of the S. typhimurium asd gene. The araC-P$_{BAD}$ was obtained from the plasmid pBAD18 (Guzman et al. (1995)) |
| pYA232 | Tc$^r$, lacI$^q$ repressor on pSC101 vector |
| pYA248 | p15A Asd$^+$ expression vector, using S. mutans asd gene (Nakayama et al. 1988). |
| pYA292 | p15A Asd$^+$ expression vector, using S. typhimurium asd gene (Galan et al. 1990). |
| pYA810 | p15A Asd$^+$ expression vector, using S. typhimurium asd gene. Derived from pYA292 by removing the HindIII fragment of the multiple cloning site containing the lacZα gene. |

F. Microbial Hosts

Any bacteria in which an essential gene is known for which mutants can be made, or for which a lethal gene is available, can serve as the host for an Environmentally Limited Viability System. Generally, those bacteria that are normally found in a target environment would be used in an Environmentally Limited Viability System targeted to that environment. It is preferred that promoters and regulatory elements of the system be native for the host being used, but this is not required. For example, many bacterial promoters are functional in heterologous hosts. Preferred host cells useful in, or useful for constructing, Environmentally Limited Viability Systems are listed in Tables 1 and 3.

1. Obtaining defective mutants. Defective mutants can be obtained as described above. For example, deletion mutations in the asd gene (Δasd) can be made in a diversity of bacterial strains that are members of the Enterobacteriaceae, and in other gram-negative bacteria and mycobacteria. *E. coli* K-12 and *S. typhimurium* LT-2 strains can be used to isolate asd mutants and their derivatives; the Asd⁻ strains can be used to construct other strains, utilizing transposon techniques, as described infra. Asd⁻ strains are also described in U.S. Pat. No. 4,190,495.

Standard mutagenesis and mutant enrichment protocols are not efficient for the recovery of asd mutants, since a mutant with a requirement for DAP undergoes lysis and death in the absence of DAP. In a synthetic medium, asd mutants require L-methionine, L-threonine, and DAP for growth. The requirement for L-methionine and L-threonine is satisfied by homoserine, which is a common precursor to both methionine and threonine. Mutagenesis of an *E. coli* or *S. typhimurium* strain followed by an ampicillin-cycloserine procedure for the enrichment of auxotrophic mutants seldom, if ever, recovers mutants with a sole requirement for homoserine. Curtiss et al. (1965) describe a cycloserine-enrichment procedure for selecting auxotrophs. The reason that homoserine-requiring auxotrophs are seldom isolated is that β-aspartic semialdehyde is converted to homoserine by either of two dehydrogenases which are encoded in two genes. The probability of inactivating both genes in a single cell is exceedingly small, and thus the homoserine-requiring auxotrophs may not be detected by random screening techniques.

This problem is overcome by the inclusion of DAP in all media during mutagenesis, and by enrichment or selection using the ampicillin-cycloserine technique. This leads to the recovery of asd mutants that require both homoserine and DAP. Ampicillin and cycloserine both inhibit cell wall synthesis in growing cells capable of protein synthesis, but are without effect on auxotrophic mutants unable to synthesize proteins because of the absence of nutritional requirements. asd mutant strains χ3008 and χ2108, which are *S. typhimurium* and *E. coli* strains, respectively, were isolated using this procedure. The Asd⁻ phenotype of χ3008 is due to a point mutation in the asd gene, and thus the frequency of reversion to Asd⁺ is fairly high. On the other hand, the Asd⁻ phenotype of χ2108 results from a deletion in the asd gene, thus, the reversion frequency is very low. Deletions within the purA gene can be obtained by isolating PurA⁺ clones from a representative library of *S. typhimurium* DNA introduced into a known *E. coli* purA mutant and selecting for growth on a defined media lacking purines. The PurA⁺ clone can then be modified to produce a deletion internal to the purA gene using either restriction enzyme digestion or inverse PCR. Following construction of the defined deletion, the modified fragment can be transferred to a suicide vector, such as pMEG-011, and subsequently introduced into the chromosome of the desired Salmonella strain using standard methods.

Figure 2:
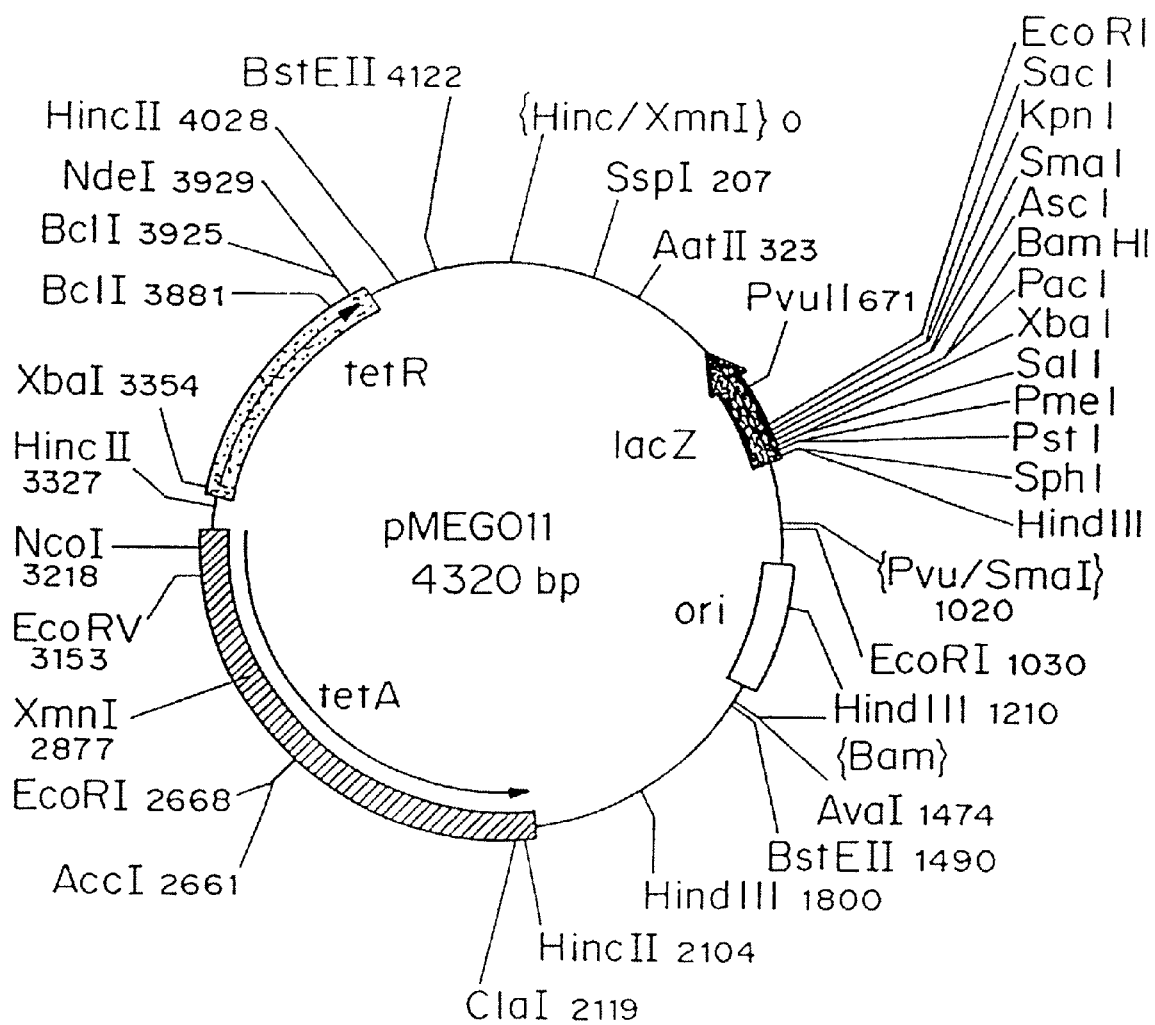
FIG. 2 is a diagram of pir-dependent suicide vector pMEG-011 which is unable to replicate in any host lacking a functional pir gene. The vector contains the multiple cloning site from the commercially available cloning vector pNEB193, providing a number of unique cloning sites and the blue/white screen associated with the lacZ α gene in an appropriate host. The vector also contains the tetracycline resistance gene (tetA) from transposon Tn10, allowing selection for tetracycline resistance with integration into the chromosome and then selection against the integrated vector on media containing fusaric acid, facilitating replacement of wild-type genes with modified genes containing deletions and insertions.

Deletion mutations containing insertions of foreign genes encoding regulatory elements for an ELVS can be introduced into the bacterial chromosome using well known recombinant DNA techniques. For example, the gene to be deleted should first be cloned onto a suicide vector such as pMEG-011 (FIG. 2). pMEG-011 is a pir-dependent suicide vector derived from pGP704 (Miller et al., *J. Bacteriol.* 170:2575–2583 (1988)). The replication of such a suicide vector is dependent on the production of a functional pir gene product by the host strain. When the suicide vector is transferred to a strain lacking the pir gene, the only means of maintaining the suicide vector is by recombination integrating the suicide vector into the host chromosome. The presence of the gene to be deleted on the suicide vector results in homologous recombination of the suicide vector into the corresponding gene on the chromosome. This integration will result in a deletion in the gene of interest if the wild-type gene on the suicide vector has been altered by deletion of internal regions of the gene prior to integration. This can be accomplished by either restriction enzyme digestion or inverse PCR amplification. The vector-borne gene of interest is thus inactivated while leaving sufficient flanking DNA to allow recombination into the chromosome. The defined deletion produced in the suicide vector can be designed to provide a convenient restriction enzyme cloning site allowing the insertion of any foreign gene, including the regulatory genes needed for the Environmentally Limited Viability System. After the initial single recombination event integrating the suicide vector into the chromosome, a second recombinational event can be selected for by selection against the tetracycline element of the suicide vector on media containing fusaric acid (Bochner et al., *J. Bacteriol.* 143:926 (1980)). Alternative mobilizable suicide vectors are also available utilizing sucrose counter selection for the introduction of defined deletions into Salmonella and other gram negative bacteria (Kaniga et al., *Gene* 109:137–141 (1991)). This results in the replacement of the wild-type allele with the deleted gene containing the desired insert. These methods have been used to produce defined deletions and insertion of foreign genes into the chromosome of Salmonella strains (Chatfield et al., *Vaccine* 10:53–60 (1992)).

Although the preferred embodiment of the disclosed ELVS is a live bacterial antigen delivery system, the ELVS can be used with any microbe in which ELVS components, as described above, can be obtained and adapted to that microbe. In particular, an ELVS will be useful when used in conjunction with the production of valuable products in fermenters, especially products that might be toxic or otherwise harmful if the bacteria producing them escaped and survived.

2. Live bacterial antigen delivery systems. Preferred hosts for use as antigen delivery systems are enteric bacteria. As used herein, the terms antigen delivery system and antigen delivery microorganism refer to a microorganism that produces an antigen or that harbors a transfer vector encoding an antigen. As used herein, enteric bacteria refers to any Enterobacteriaceae. Many of the preferred genes and regulatory elements described above are operable in most enteric bacteria, thus allowing use of the many well developed *E. coli* and Salmonella regulatory systems. Most preferably, the bacterial host is an avirulent Salmonella.

In one embodiment of the system described herein, an avirulent derivative of a pathogenic microbe that attaches to, invades and persists in the gut-associated lymphoid tissue (GALT) or bronchial-associated lymphoid tissue (BALT) is used as a carrier of the gene product which is used for stimulating immune responses against a pathogen or allergen. Avirulent does not mean that a microbe of that genus or species can not ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Avirulent Salmonella containing an ELVS can be used to protect animals and humans against Salmonella infection. To be useful, such strains need not express any foreign antigen. Recombinant avirulent Salmonella expressing protective antigens from bacterial, viral, mycotic and parasitic pathogens that are efficacious in inducing immunities to protect against infections by these pathogens will be more acceptable and receive more widespread use if rendered safer by biological containment properties that preclude survival and proliferation in the environment.

Shigella or an enteroinvasive *E. coli* can be useful in antigen delivery systems since invasion into colonic mucosa could stimulate lymphoid tissues adjacent to the colon, so as to stimulate a strong mucosal immune response in the reproductive tract. Rectal immunization can be effective because of anatomical features such as the proximity of lymph nodes and lymphatics to the colon.

3. Avirulent Bacterial Hosts. To be useful for delivery of an expression product, such as an antigen, the bacterial host must be avirulent. Strains of different Salmonella serotypes can be rendered avirulent and immunogenic by methods known to those skilled in the art, for example, 1) by introducing mutations that impose a requirement for aromatic amino acids and vitamins derived from precursors in this pathway (Stocker et al. (1983), Hoiseth and Stocker (1981)), 2) by mutating genes for global regulators such as cya and crp (Curtiss and Kelly (1987)), phoP (Miller et al., *Proc. Natl. Acad. Sci. USA* 86:5054–8 (1989), Galan and Curtiss, *Microb. Pathogen.* 6:433–443 (1989)), and ompR (Dorman et al., *Infect. Immun.* 57:2136–40 (1989)), 3) by mutating genes for lipopolysaccharide (LPS) synthesis, such as by galE (Germanier and Furer, *Infect. Immun.* 4:663–73 (1971), Germanier and Furer, *J. Infect. Dis.* 131:553–8 (1975)), although this alone may be insufficient (Hone et al., *Infect. Immun.* 56:1326–1333 (1988)), 4) by mutating genes needed for colonization of deep tissues, such as cdt (Kelly et al., *Infect. Immun.* 60:4881–4890 (1992); Curtiss et al., *Devel. Biol. Stand.* 82:23–33 (1994)), or 5) by preventing expression of genes for proteases required at high temperature, such as htrA (Johnson et al., *Mol. Microbiol.* 5:401–407 (1991). Strains possessing mutations in phoQ (Miller et al., Proc. Natl. Acad. Sci. USA 86:5054 (1989)) have the same phenotype as mutations in phoP. Hereinafter strains with mutations in either phoP or phoQ are referred to collectively as phoP mutants. It is preferred that mutations in the above described genes be introduced as deletions since this will preclude reversion mutations and enhance the safety of the strains containing them. Subsequent to the discovery that Salmonella strains with mutations in the genes described above are avirulent and immunogenic, it was observed that many of these strains exhibited, after oral administration, nearly wild-type abilities to invade and persist in the GALT and to colonize other lymphoid tissues such as mesenteric lymph nodes, liver, and spleen, but without causing disease symptoms. As a consequence, these attenuated strains are capable of stimulating strong mucosal, systemic and cellular immune responses in immunized animal hosts that confer protective immunity to challenge with virulent wild-type Salmonella strains. Any of these avirulent Salmonella can be endowed with the ability to express important colonization or virulence antigens from other bacterial, viral, mycotic and parasitic pathogens at a high level within an immunized animal host (Clements, *Pathol. Immunopathol. Res.* 6:137–146 (1987); Dougan et al., *Parasite Immun.* 9:151–60 (1987); Chatfield et al., *FEMS Immunol. Med. Microbiol.* 7:1–7 (1993); Curtiss et al., in *Virulence mechanisms of bacterial pathogens,* (Roth, American Society for Microbiology, Washington, D.C., 1988) pages 311–328; Curtiss et al., *Dev. Biol. Stand.* 82:23–33 (1994); Doggett and Curtiss, *Adv. Exp. Med. Biol.* 327:165–73 (1992); Schodel, *Semin Immunol.* 2:341–9 (1990)).

4. Reduced survivability. Environmentally Limited Viability System can also be used in host strains that exhibit reduced survival in certain environments. A preferred form of this is present in relA mutant strains. Although the specific factor responsible for the reduced survival of the relA mutations is not known, the pleiotropic effects of relA mutations, including membrane ruptures and incorrect amino acid incorporation into proteins, can reduce the survival of relA mutants in any amino acid limiting environment. Such a reduction in survival of relA mutants has been demonstrated in limiting environments for both *E. coli* (Hecker et al., *Arch Microbiol.* 143:400–402 (1986)), and *S. typhimurium* (Spector and Cubitt, *Mol. Micro.* 6:1467–1476 (1992)). Decreased survival of *E. coli* strains with a relA mutation was also observed by Schweder et al., *Appl. Microbiol. Biotechnol.* 42:718–723 (1995). A ΔrelA mutation in *S. typhimurium* had no appreciable effect on virulence.

G. Expression Genes

One of the primary uses of the disclosed Environmentally Limited Viability System is to allow recombinant expression of a desired expression product limited to a specific permissive environment. As used herein, expression gene refers to a gene expressed in an ELVS that encodes a desired expression product. Expression of a gene means that the information inherent in the structure of the gene (the sequence of DNA bases) is transformed into a physical product in the form of an RNA molecule, polypeptide or other biological molecule by the biochemical mechanisms of the cell in which the gene is located. The biological molecule so produced is called the expression product. The term expression product as used here refers to any biological product or products produced as a result of the biochemical reactions that occur under the control of a gene. The expression product may be, for example, an RNA molecule, a peptide, or a product produced under the control of an enzyme or other molecule that is the initial product of the gene, that is, a metabolic product. Such expression products need not be heterologous to the host cell nor encoded by a recombinant gene. It is preferred, however, that the expression gene is recombinant. It is preferred that expression genes encode antigens, enzymes, toxins, immunomodulators, adjuvants, and cytotoxic proteins. Most preferably, the expression gene encodes an antigen.

Expression of the expression gene can occur either in the microorganism containing an Environmentally Limited Viability System, or in a cell of a host animal to which the microorganism has been administered. In the latter case, the expression gene is preferably on a transfer vector for transfer to host animal cells. Expression of the expression gene can be accomplished, for example, by inserting the coding sequence encoding a desired gene product in the multiple cloning site of the ELVS vector pMEG-104 (FIG. 4). This places the coding sequence of the expression gene under control of the constitutive promoter Ptrc, with transcription terminating at rrnB thus preventing inappropriate transcription of the lysis genes.

Antigens. Live recombinant microorganisms using an Environmentally Limited Viability System can be used to deliver any product that can be expressed in the host microorganism. Preferred expression products for this purpose are antigens. For example, antigens can be from bacterial, viral, mycotic and parasitic pathogens, to protect against bacterial, viral, mycotic, and parasitic infections, respectively; gametes, provided they are gamete specific, to block fertilization; and tumor antigens, to halt cancers. It is specifically contemplated that antigens from organisms newly identified or newly associated with a disease or pathogenic condition, or new or emerging pathogens of animals or humans, including those now known or identified in the future, can be used in an Environmentally Limited Viability System. Antigens for use in an ELVS are not limited to those from pathogenic organisms. The selection and recombinant expression of antigens has been previously described by Schodel (1992) and Curtiss (1990). Immunogenicity of the microorganisms can be augmented and/or modulated by constructing strains that also express genes for cytokines, adjuvants, and other immunomodulators.

Some examples are microorganisms useful as a source for antigen are listed below. Theses include microoganisms for the control of plague caused by *Yersinia pestis* and other Yersinia species such as *Y. pseudotuberculosis* and *Y. enterocolitica,* of gonorrhea caused by *Neisseria gonorrhoea,* of syphilis caused by *Treponema pallidum,* and of venereal diseases as well as eye infections caused by *Chlamydia trachomatis.* Species of Streptococcus from both group A and group B, such as those species that cause sore throat or heart diseases, *Neisseria meningitidis, Mycoplasma pneumoniae* and other Mycoplasma species, *Hemophilus influenza, Bordetella pertussis, Mycobacterium tuberculosis, Mycobacterium leprae,* Bordetella species, *Escherichia coli, Streptococcus equi, Streptococcus pneumoniae, Brucella abortus, Pasteurella hemolytica* and *P. multocida, Vibrio cholera,* Shigella species, Borrellia species, Bartonella species, *Heliobacter pylori,* Campylobacter species, Pseudomonas species, Moraxella species, Brucella species, Francisella species, Aeromonas species, Actinobacillus species, Clostridium species, Rickettsia species, Bacillus species, Coxiella species, Ehrlichia species, Listeria species, and *Legionella pneumophila* are additional examples of bacteria within the scope of this invention from which antigen genes could be obtained. Viral antigens can also be used with the Environmentally Limited Viability System. Viral antigens can be used in antigen delivery microorganisms directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, or Retrovirus. Antigen delivery microorganisms using antigens of pathogenic fungi, protozoa and parasites can also be used.

The antigen can also be an allergen of the host such as antigens from pollen and animal dander. Such an antigen can be used in the Environmentally Limited Viability System in an exposure regimen designed to specifically desensitize an allergic host.

Recombinant avirulent Salmonella are capable of stimulating strong mucosal, systemic and cellular immune responses against the foreign antigens and thus against the pathogen that is the source of the foreign antigen. It is not necessary that the antigen gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus a gene as defined and claimed here is any unit of heredity capable of producing an antigen. The gene may be of chromosomal, plasmid, or viral origin.

Multiple antigens can also be expressed by a recombinant avirulent Salmonella strain. In addition, antigens, or even parts of antigens, that constitute a B cell epitope or define a region of an antigen to which an immune response is desired, can be expressed as a fusion to a carrier protein that contains a strong promiscuous T cell epitope and/or serves as an adjuvant and/or facilitates presentation of the antigen to enhance, in all cases, the immune response to the antigen or its component part. This can easily be accomplished by genetically engineering DNA sequences to specify such fusions for expression by avirulent strains. Fusion to tenus toxin fragment C, CT-B, LT-B and hepatitis virus B core are particularly useful for these purposes, although other epitope presentation systems are well known in the art.

In order for the expression gene to be effective in eliciting an immune response, the expression gene must be expressed, which can be accomplished as described above. In order for an antigen delivery microorganism to be effective in immunizing an individual, the antigenic material must be released in such a way that the immune system of the vaccinated animal can come into play. Therefore the live avirulent microorganism must be introduced into the animal. In order to stimulate a preferred response of the GALT or BALT cells as discussed previously, introduction of the microbe or gene product directly into the gut or bronchus is preferred, such as by oral administration, intranasal administration, gastric intubation or in the form of aerosols, although other methods of administering the antigen delivery microorganism, such as intravenous, intramuscular, subcutaneous injection or intramammary, intrapenial, intrarectal, or vaginal administration, is possible.

H. Microorganism Compositions

Microorganisms containing an Environmentally Limited Viability System can be administered to animal hosts. Such microorganisms can be used to deliver expression products such as antigens or transfer vectors as described elsewhere herein. For this purpose, it is preferred that the microorganism be formulated in a composition suitable for administration.

Antigen Delivery Compositions. A preferred use of antigen delivery microorganisms is as vaccines for stimulating an immune response to the delivered antigens. Oral immunization in a suitable animal host with live recombinant Salmonella vaccine strains leads to colonization of the gut-associated lymphoid tissue (GALT) or Peyer's patches, which leads to the induction of a generalized mucosal immune response to both Salmonella antigens and the foreign antigens synthesized by the recombinant Salmonella (Curtiss et al., *Adv. Exp. Med. Biol.* 251:33–47 (1989)). Further penetration of the vaccine strain into the mesenteric lymph nodes, liver and spleen augments the induction of systemic and cellular immune responses directed against Salmonella antigens and the foreign antigens made by the recombinant Salmonella (Doggett and Curtiss (1992)). Thus the use of recombinant avirulent Salmonella vaccines for oral immunization stimulates all three branches of the immune system, particularly important when immunizing against infectious disease agents which colonize on and/or invade through mucosal surfaces.

By vaccine is meant an agent used to stimulate the immune system of a living organism so that an immune response occurs. Preferably, the vaccine is sufficient to stimulate the immune system of a living organism so that protection against future harm is provided. Immunization refers to the process of inducing a continuing high level of antibody and/or cellular immune response in which T-lymphocytes can either kill the pathogen and/or activate other cells (for example, phagocytes) to do so in an organism, which is directed against a pathogen or antigen to which the organism has been previously exposed. Although the phrase "immune system" can encompass responses of unicellular organisms to the presence of foreign bodies, that is, interferon production, as used herein the phrase is restricted to the anatomical features and mechanisms by which a multi-cellular organism responds to an antigenic material which invades the cells of the organism or the extra-cellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals, although the vaccines described herein are not limited to those which stimulate IgA production. For example, vaccines of the nature described herein are likely to produce a broad range of other immune responses in addition to IgA formation, for example, cellular and humoral immunity. Immune responses to antigens are well studied and widely reported. A survey of immunology is given in Barrett, *Textbook of Immunology,* Fourth Edition, (C. V. Mosby Co., St. Louis, Mo., 1983), Sites et al., *Basic and Clinical Immunology* (Lange Medical Books, Los Altos, Calif., 1994), and Orga et al., Handbook of Mucosal Immunology (Academic Press, San Diego, Calif., 1994). Mucosal immunity is also described by McGhee and Mestecky, *The Secretory Immune System,* Ann. N.Y. Acad. Sci., Volume 409 (1983).

An individual treated with a vaccine of the invention is defined herein as including all vertebrates, for example, mammals, including domestic animals and humans, various species of birds, including domestic birds, particularly those of agricultural importance. Preferably, the individual is a warm-blooded animal.

The dosages of live recombinant vaccines required to elicit an immune response will vary with the antigenicity of the cloned recombinant expression product and need only be a dosage sufficient to induce an immune response typical of existing vaccines. Routine experimentation will easily establish the required dosage. Typical initial dosages of vaccine for oral administration could be $1 \times 10^7$ to $1 \times 10^{11}$ CFU depending upon the size and age of the individual to be immunized. Administering multiple dosages can also be used as needed to provide the desired level of protective immunity. The pharmaceutical carrier in which the vaccine is suspended can be any solvent or solid material for encapsulation that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc or sucrose, or animal feed. Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

Although it is preferred that antigen delivery microorganisms be administered by routes that stimulate a mucosal immune response, namely oral, intranasal, intravaginal, and interrectal, these microorganisms can also be delivered intramuscularly, intravenously, and in other parenteral routes. Administration of an antigen delivery microorganism can also be combined with parenteral administration of purified antigenic components. In case where an ELVS is used to control or treat cancer, it is preferred that the ELVS be administered parenterally.

I. Adaptation of Environmentally Limited Viability Systems to Useful Host Strains Avirulent strains of *S. typhimurium* are known to be totally attenuated and highly immunogenic in mice, chickens, and pigs, inducing protective immunity to infection with 10,000 times a lethal dose with the virulent wild-type strain. Similarly, avirulent strains of *S. choleraesuis* are attenuated and immunogenic in mice and pigs and also offer significant protective immunity. Avirulent strains of *S. dublin* have been isolated and tested and found to be avirulent, immunogenic, and protective in calves. Attenuated *S. typhi* strains have also been constructed and found to induce significant immune responses in human volunteers. Attenuated derivatives of *Vibrio cholerae* and *Shigella flexneri* have also been constructed and used as vaccines to induce significant immune responses in human volunteers. *Mycobacterium bovis* strain BCG has also been used to orally immunize humans. Attenuated *Listeria monocytogenes* has also been used as a live vaccine for immunization of mice. In addition to serving as vaccines to immunize animals and human hosts against infection with related virulent wild-type strains, avirulent derivatives of the above cited microorganisms can also be used as antigen delivery vectors by genetically engineering them to express foreign antigens. These antigens could be from bacterial, viral, fungal and parasitic pathogens or they could be allergens or they could be gamete specific antigens in a contraceptive vaccine or tumor antigens in anti cancer vaccines. Immunization of animal and/or human hosts with these live recombinant avirulent vaccines is known to induce mucosal, systemic and cellular immune responses directed against the foreign antigen and against the pathogen from which the gene specifying the foreign antigen was isolated or against allergens or against sperm or ova or against tumor cells, respectively.

Bacterial pathogens can be attenuated by introducing deletion (Δ) mutations in various genes as described above or as known to those knowledgeable in the art. Any of these strains are suitable for introduction of an ELVS of the sort disclosed herein, although modifications would be needed to make the system operable in gram-positive bacteria. Specifically these modifications would require modification of Shine-Dalgarno sequences to permit translation of mRNA, slight changes in promoter sequences to cause transcription to be more efficient, and, in the case of all gram-positive genera other than Mycobacteria, the asd gene would need to be replaced by some other essential gene. This is because DAP is not contained in the rigid layer of the cell wall of most gram-positive bacterial genera except for the Mycobacteria. On the other hand, there are numerous essential genes for essential components of the cell wall, cell membranes, and for maintaining the integrity of DNA that could be used in both gram-positive and gram-negative bacteria. The components of the ELVS described in FIG. 4 can readily be introduced into Salmonella species, E. coli, Shigella species and other enterics. For example the suicide vector pMEG-096, can be transferred from a pir-containing donor strain to an attenuated vaccine candidate with a wild-type asd gene. Integration of the cI857PRc2 cartridge of pMEG-096 into the candidate strain can be accomplished by first selecting tetracycline resistant clones that have integrated pMEG-096, and then growing the cells on fusaric acid-containing media to select for cells that have lost the wild-type asd gene in favor of the asd defined deletion containing the cI857PRc2 cartridge. These manipulations are described in the examples below. A derivative of pMEG-104 (FIG. 4) containing a gene encoding a desired foreign antigen, could then be introduced by electroporation. The resulting recombinant avirulent vaccine with its ELVS can then be used to immunize suitable hosts. Excretion or shedding of any live vaccine cells by the vaccinated hosts will activate the ELVS which will lead to death by lysis of these vaccine cells. This will preclude the survival of the vaccine outside of th& host animal and thus eliminate the possibility for immunization of individual hosts that did not elect to be immunized.

Deposits of Strains Useful in Practicing the Invention.

A deposit of biologically pure cultures of the following strains (Table 3) were made with the American Type Culture Collection, 12301 Parklawn Drive, Rockville, Md. The accession number indicated was assigned after successful viability testing, and the requisite fees were paid. Access to the cultures will be available during pendency of the patent application to one determined by the Commissioner to be entitled thereto under 37 CFR 1.14 and 35 USC 122. All restriction on availability of the cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, loose its plasmid, it will be replaced with a viable culture(s) of the same taxonomic description.

TABLE 3

Strains Deposited with ATCC for Implementation of Environmentally Limited Viability System

| Strain (plasmid) | ATCC No. | Deposit Date | Description | Genotype |
| --- | --- | --- | --- | --- |
| MGN-318 (pMEG-096) | 69835 | Jun. 6, 1995 | E. coli MGN-026 containing pMEG-096. pMEG-096 (FIG. 3) contains the λP$_R$ driven P22 c2 repressor gene and λcI857 repressor gene on a 2.05 kb ClaI fragment from pMEG-088 treated with T4 DNA polymerase and ligated into the BglII site of the asd deletion vector pMEG-006 following treatment with T4 DNA polymerase and CIAP. This provides the λP$_R$ driven P22 c2 gene and λcI857 repressor gene between either end of the S. typhimurium asd deletion allowing insertion into the chromosome. | (pMEG-096 Δasd-17:: cI857PRc2) endA1 hsdR17 (rk−, mk+) supE44 thi-1 recA1 gyrA relA1 Δ(lacZYA-argF) U169 λpir deoR (φ80dlac Δ(lacZ)M15) |
| MGN-392 | 55693 | Jun. 6, 1995 | S. typhimurium UK-1 ELVS host obtained from MGN-377 by selecting for fusaric acid resistant, tetracycline sensitive, Asd⁻ isolates produced by excision of pMEG-096 in MGN-377 leaving the cI857PRc2 cartridge in the defined asd deletion. | Δasd-17:: cI857PRc2 |
| MGN-417 (pMEG-104) | 69836 | Jun. 6, 1995 | S. typhimurium UK-1 ELVS host MGN-392 electroporated with the ELVS expression vector, pMEG-104 (FIG. 4), an asdlysis p15A expression vector obtained by deleting the 1.36 kb SalI fragment of pMEG-100 (Table 2, FIG. 5) containing the Km$^r$ cartridge. This construct does not grow at temperatures below 30° C. Plasmid requires host with functional P22 c2 gene. | (pMEG-104 P22P$_R$ lys13 lys19 asd λp$_L$) Δasd-17:: cI857PRc2 |

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLES

Example 1
Construction of a Plasmid Based Thermoregulated Environmentally Limited Viability System The methods used to produce the components of the ELVS illustrated in FIG. 4 employed standard molecular cloning techniques. The ELVS depicted in FIG. 4 consists of two main components. The first component is the ELVS vector which combines the application of a temperature regulated essential gene, asd, with the temperature regulated lethal genes, lys13 and lys19, oriented in a manner to provide additional regulation by antisense RNA for both essential and lethal genes. The second component is the ELVS host required to maintain the ELVS vector, which for the *S. typhimurium* examples used the host MGN-392, possessing a defined asd deletion with a thermosensitive cI857 and c2 repressor cartridge insert.

The ELVS expression vector pMEG-104, was constructed by the assembly of six individual components consisting of 1) the *S. typhimurium* asd gene, 2) the bacteriophage lambda promoter left to drive the asd gene, 3) the bacteriophage P22 lysis genes lys13 and lys19, 4) the bacteriophage P22 promoter right to drive the lysis genes, 5) the trpA terminator to prevent transcription from external promoters, and 6) the expression vector core obtained from pYA810 (Galan et al. (1990)), consisting of the p15A origin of replication, the strong trc promoter, multiple cloning site used in existing Asd+ vectors, and the ribosomal transcription terminators 5S T1 T2 to prevent transcriptional interference from the trc promoter. Many of these vector components were obtained by PCR amplification as described below, followed by modification of the DNA ends with either restriction enzymes or polymerases to allow assembly of the intermediate constructs. The asd gene of *S. typhimurium* was obtained by PCR amplification of the region between nucleotides 314 to 1421 of the *S. typhimurium* asd sequence as found on pYA292 (Galan et al. (1990)). This asd PCR product, a 1115 bp fragment with one end blunt and the other having a BglII overhang and lacking the promoter and Shine-Dalgarno regions of the asd gene, was cloned into the lambda promoter left vector, pMEG-076, in an orientation to produce an asd gene driven by the bacteriophage lambda promoter left. The result is plasmid pMEG-086.

The promoter left of bacteriophage lambda present on pMEG-076 was obtained by PCR amplification of the region between nucleotides 5 to 160 of the promoter left sequence (Giladi et al., *J. Mol. Biol.* 231:109–121 (1990)). The resulting 155 bp fragment, with a blunt end and a BamHI end, was cloned into the SmaI to BamHI sites of the promoter probe cloning vector pKK232-8 (Brosius, J. *Gene* 27:151 (1984)), resulting in vector pMEG-086. In this vector, the asd gene is driven by the lambda promoter left.

The 1277 bp EcoRI to XbaI fragment of pMEG-086 containing the $\lambda P_L$ driven asd gene was then sub-cloned into the PvuII to XbaI sites of the bacteriophage P22 PR lys13 lys19 vector pMEG-089 using a synthetic trpA terminator, containing an internal BglII site and an EcoRI end, to produce pMEG-097. The relative orientation of the transcriptional elements for asd and lys13 lys19 in pMEG-097 results in convergent transcription which produces antisense RNA for the asd and lys genes at differential temperatures.

The bacteriophage P22 lysis genes used in the construction of pMEG-097 were obtained by PCR amplification of nucleotides 62 to 850 of the P22 lysis gene region (Rennell et al., *Virology* 142:280–289 (1985)). The resulting 797 bp fragment, with an introduced Shine-Dalgarno site, a 5' blunt end, and a PstI site designed into the 3' end, was cloned into the EcoRV to PstI sites of the low copy-number vector pWKS30 (Kushner, S. *Gene* 100:195–199 (1990)). The resulting vector, pMEG-078, has the lys13 and lys19 genes under control of the lac promoter. The lysis genes were then sub-cloned as a 1060 bp SalI to PvuII fragment from pMEG-078 into the SalI to PvuII sites of the P22 promoter right expression vector, pMEG-072. In the resulting vector, pMEG-089, the bacteriophage P22 lysis genes lys13 lys19 are driven by the P22 promoter right. The bacteriophage P22 promoter right in pMEG-072 was obtained by PCR amplification of the region between nucleotides 23 and 138 of the P22 promoter right sequence (Poteete et al., *J. Mol. Biol.* 137:81–91 (1980)). The resulting 125 bp BamHI to SalI fragment was cloned into the BamHI to SalI sites of the promoter probe vector pKK232-8 (Brosius, J., *Gene* 27:151 (1984)) to produce pMEG-072.

The asd lys13 lys19 cartridge present in pMEG-097 contains both the essential and lethal genes separated by a portion of the multiple cloning site, including a BamHI site from previous manipulations. This region was deleted from pMEG-097 as a 28 bp PstI-XbaI fragment, and the remaining vector was treated with T4 DNA polymerase prior to religating. This resulted in vector pMEG-098, containing the asd lys13 lys19 cartridge. The asd lys13 lys19 cartridge was then transferred to the expression vector core of pMEG-090 by digesting pMEG-090 with BglII and inserting the 2.26 kb BamHI to BglII fragment of pMEG-098 containing the asd lys13 lys19 cartridge. This produced pMEG-100, shown in FIG. 5.

Vector pMEG-090 was derived from pYA810 by performing a partial BglII digest of pYA810; isolating the 1.6 kb fragment of pYA810 containing the p15A origin of replication, the trc promoter, and the multiple cloning site with the transcriptional terminator; and ligating the fragment to the 1.3 kb BamHI kanamycin resistance element of pUC-4K (Christie G. E., et al., *Proc. Natl. Acad. Sci. USA* 78:4180 (1981)).

In pMEG-100, the essential and lethal genes are flanked by two different transcriptional terminators, the first is the trpA terminator (Christie et al., *Proc. Natl. Acad. Sci. USA* 78:4180 (1981)) and the other is the ribosomal 5S terminator repeat cartridge used in the previously described Asd+ balanced-lethal vectors pYA248 and pYA292 (EP 89900028.5). Vector pMEG-100 also contains the lower copy-number DNA polymerase I-dependent p15A origin of replication and the strong trc promoter derived from pYA810 and used in the pYA292 Asd+ vector described in EP 89900028.5. The kanamycin resistance element of pMEG-100 was then removed by a partial SalI digest to produce pMEG-104, the ELVS vector shown in FIG. 4.

The second component of the ELVS is the host strain containing the regulator elements responsible for the response of the modified bacteria to the environmental conditions encountered. In the present example the host is MGN-392 or the sibling strain MGN-391, which contain a cI857PRc2 cartridge. The cI857PRc2 cartridge contains the bacteriophage lambda promoter right driven bacteriophage P22 c2 repressor gene and the bacteriophage lambda temperature-sensitive repressor gene cI857. The cartridge is located between flanking portions of the *S. typhimurium* asd gene and replaces the chromosomal asd gene of the wild-type *S. typhimurium* strain $\chi 3761$. More specifically, the cI857PRc2 cartridge is a combination of a PCR amplified fragment of bacteriophage P22 derived from nucleotides 1 to 650 of the c2 gene (Sauer, R. et al., *Biochem.* 20:3591–3598 (1981), and a PCR amplified fragment of bacteriophage lambda, from nucleotides 37219 to 38035 of the lambda genome (Sanger, F., et al., *J. Mol. Biol.* 162:729–773 (1982), which contains the cI857 gene and the lambda promoter right. On the cartridge, the lambda promoter right drives expression of the P22 c2 gene. This cartridge has been inserted between the flanking portions of a defined deletion of the *S. typhimurium* asd gene lacking the portion of the asd gene between nucleotides 243 and 1460. This deletion prevents production of any β-aspartate semialdehyde dehydrogenase by the host strain MGN-392.

The function of the ELVS is demonstrated for both Salmonella and *E. coli* using the host strains MGN-392 for *S. typhimurium* (Table 3) and MGN-336 for *E. coli* (Table 1). MGN-392 was electroporated with either the Asd⁺ vector pYA292, to produce MGN401 (Table 1), or the ELVS expression vector pMEG-104, to produce MGN-417 (Table 3). MGN-336 was electroporated with the ELVS expression vector pMEG-104, to produce MGN-409 (Table 1). These strains were then grown for 12 to 16 hours in Lennox broth without aeration at 37° C. and dilutions plated onto Lennox agar followed by incubation at the temperature indicated for up to 72 hours. The plating efficiency, measured as colony forming units, observed at room temperature (25° C.) for MGN-417 is approximately 10,000 less than that observed for MGN-401, containing the Asd⁺ vector, at the same temperature. The colonies observed after room temperature incubation of *E. coli* strain MGN-409 containing the ELVS vector pMEG-104 were extremely small, indicating poor growth survival (Table 4). The reduction obtained in plating efficiency of MGN-417 at 25° C. in the presence of DAP indicates that the lysis genes are functioning alone to cause greater than 95% killing.

TABLE 4

Plating Efficiency of Strains Containing Temperature Regulated ELVS Vectors[a]

| Strain (plasmid) | L agar at 25° C. CFU at $10^{-4}$ dil. | L agar at 37° C. CFU at $10^{-7}$ dil. | L agar + DAP at 25° C. CFU at $10^{-7}$ dil. |
|---|---|---|---|
| *S. typhimurium* MGN-401 (pYA292) | >10,000 | 23 | N/A |
| *S. typhimurium* MGN-417s (pMEG-104) | 1 mucoid | 67 | 1 mucoid |
| *E. coli* MGN-409e (pMEG-104) | ~10,000 very small | 36 | N/A |

[a]Colony forming units (CFU) of cultures diluted $10^{-4}$ or $10^{-7}$ plated on L agar or L agar + DAP, after 72 hrs incubation at designated temperature.

Figure 6:
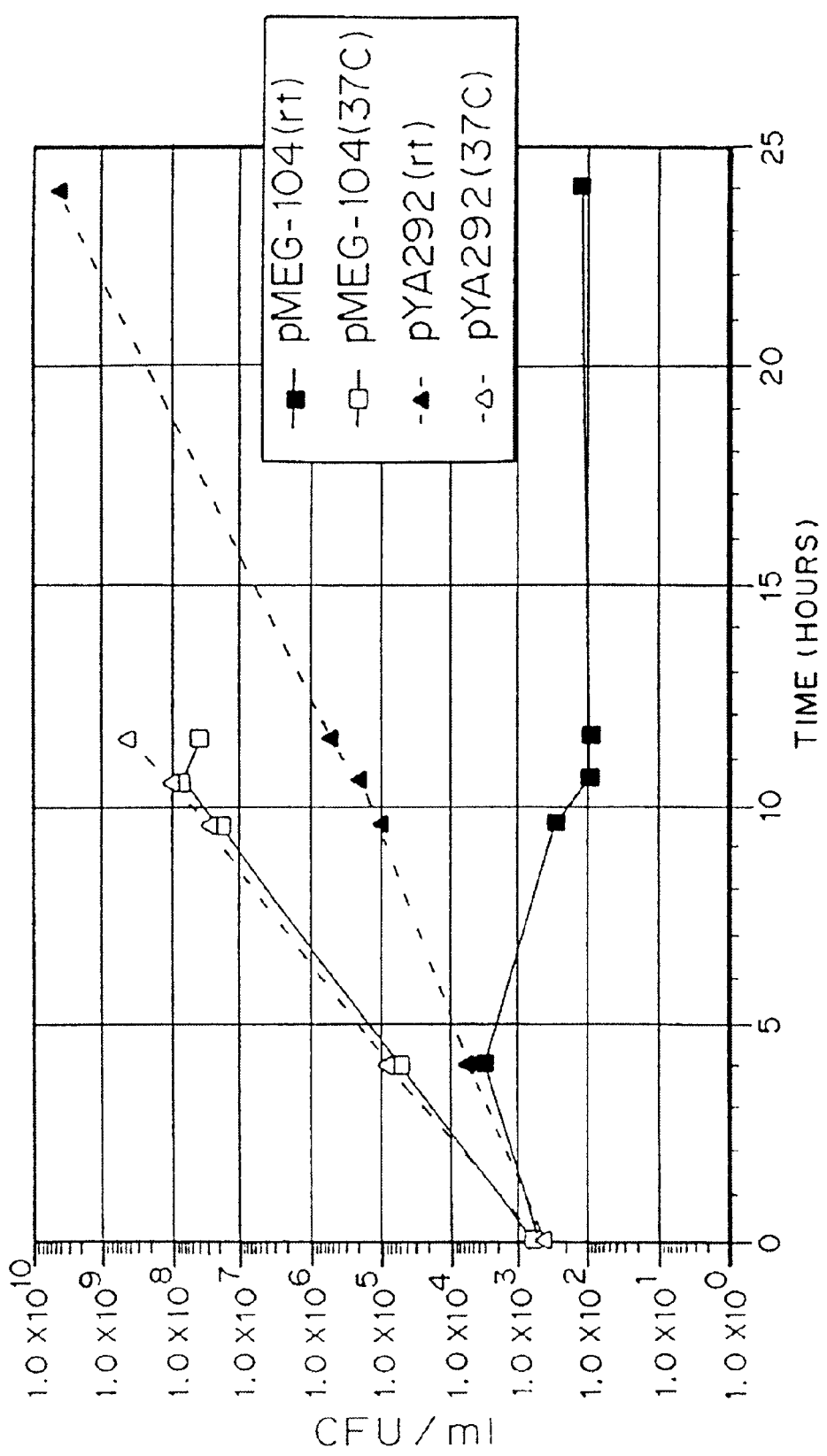
FIG. 6 is a graph of the growth (CFU/ml) versus time (hours) of *S. typhimurium* hosts with and without an Environmentally Limited Viability System. Filled squares indicate growth points of cells containing pMEG-104 grown at room temperature. Open squares indicate growth points of cells containing pMEG-104 grown at 37° C. Filled triangles indicate growth points of cells containing the Asd$^+$ vector pYA292 grown at room temperature. Open triangles indicate growth points of cells containing pYA292 grown at 37° C.

This reduction in viability is further demonstrated by the data in FIG. 6 for the Salmonella based ELVS in which MGN-417 (Table 3) fails to grow in complex liquid media at room temperature. Under these conditions, MGN-417 is unable to proliferate and exhibits a reduction in recoverable bacteria over a 24 hour period at the non-permissive temperature of 25° C., while still growing as well as MGN-401 (Table 1), the ELVS host MGN-392 containing the Asd⁺ vector pYA292, at the permissive temperature of 37° C.

Figure 5:
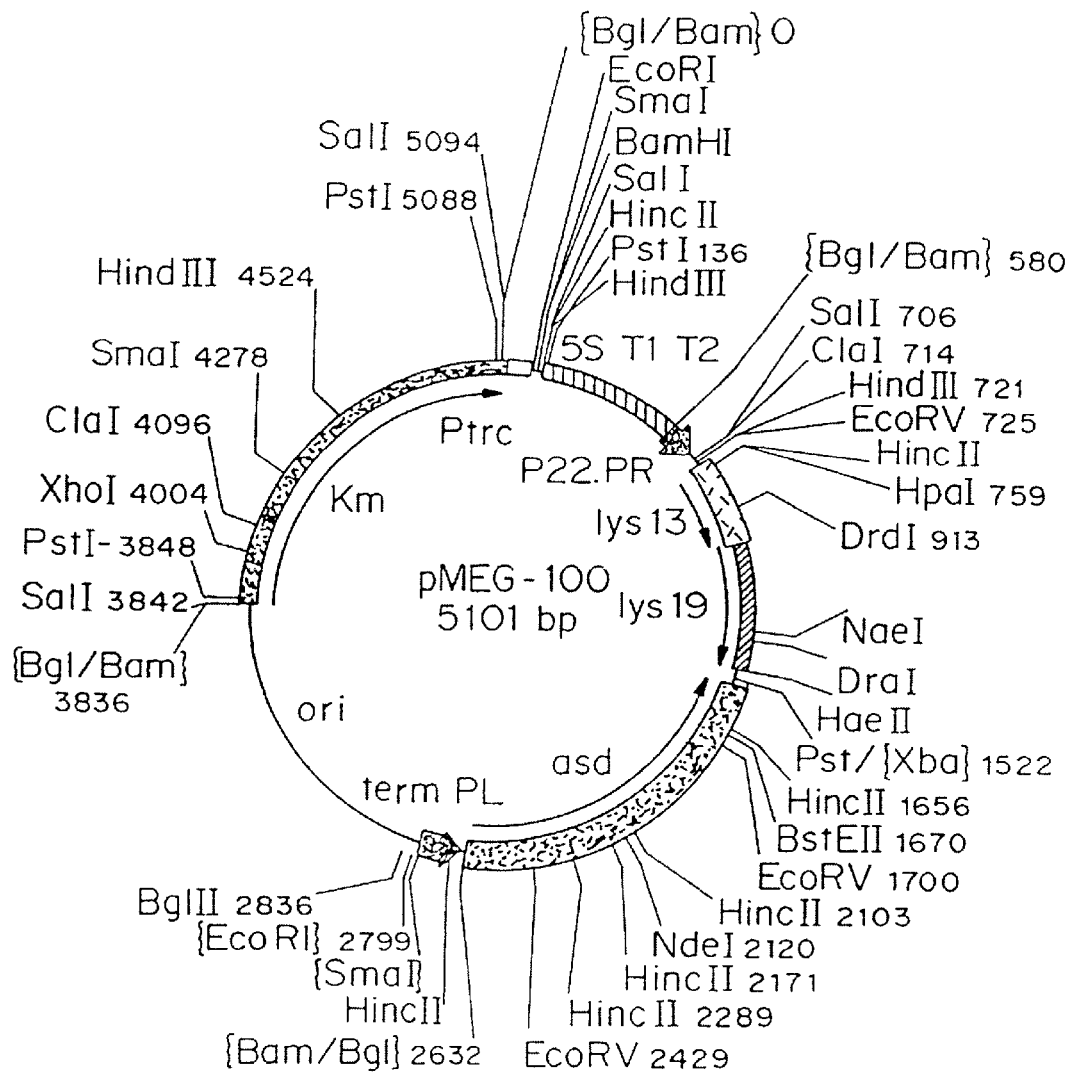
FIG. 5 is a diagram of vector pMEG-100. This vector is the same as vector pMEG-104 except that pMEG-100 contains a kanamycin resistance gene.

Example 2
Restricted Transfer of Environmentally Limited Viability Vector DNA to Other Bacterial Hosts This example demonstrates the inability of bacterial hosts not containing the cI857PRc2 cartridge to maintain the Environmentally Limited Viability System vector, even at permissive temperatures. During the construction of pMEG-104, as described earlier, the vector pMEG-100, containing a kanamycin resistance gene, was produced (FIG. 5). Vector pMEG-100 and the tetracycline resistance plasmid pYA232 were co-purified from MGN-399 (Table 1). Vector pYA232 has a low copy-number pSC101 replicon that is compatible with the p15A origin of replication present on pMEG-100. The pool of plasmid DNA isolated from MGN-399 was then electroporated into an Asd⁻ *S. typhimurium* host, χ3730, lacking the c2 repressor gene necessary for repression of the P22 lysis genes. In this strain, the lysis genes on pMEG-100 should limit the transformability by PMEG-100. The same pool of plasmid DNA was also electroporated into host strain MGN-391 (Table 1) to confirm the transformability of the DNA. The inability of the non-specific host, χ3730, to propagate the ELVS plasmid is evidenced by an approximately 3,000-fold drop in the number of electroporants obtained with pMEG-100 relative to pYA232 within the same DNA mix (Table 5). The CFU on L agar with tetracycline and DAP reveal the frequency of recovery of pYA232.

TABLE 5

Restriction of Plasmid Transfer to Non-permissive Hosts[a] (CFU at $10^{-1}$ dilution)

| Strain | DNA | LA – | LA + Tet + DAP | LA + Km |
|---|---|---|---|---|
| χ3730 | — | 0 | 0 | 0 |
| χ3730 | pMEG-100 + pYA232 | 16 | >1,000 | 4 |
| MGN-391 | — | 0 | 0 | 0 |
| MGN-391 | pMEG-100 + pYA232 | >10,000 | ~1,000 | >10,000 |

[a]a mixture of pMEG-100 and pYA232 plasmid DNAs were isolated from *S. typhimurium* MGN-399 and used to transform the bacterial strains listed by electroporation.
[b]CFU (colony forming units) were determined by incubating dilutions spread on LA (Lennox agar) plates with or without tetracycline (Tet; 15 μg/ml); diaminopimelic acid (DAP; 50 μg/ml) or kanamycin (Km; 30 μg/ml) at 37° C.

Example 3
Construction of a Temperature-Regulated polA Host

This example describes the design of a Δasd Environmentally Limited Viability System in which the effectiveness of the Environmentally Limited Viability System is further ensured by employing a temperature regulated polA gene. The chromosomal pola gene has been altered to be expressed at 37° C. but not at temperatures below 30° C., thus preventing further replication of polA-dependent replicons containing the essential asd gene at the non-permissive temperature. As described above, the replication of plasmids with the p15A, pBR and pUC origins of replication are dependent on DNA polymerase I. These replicons are widely used in cloning vectors. The inability of these polA-dependent plasmids to replicate at temperatures below 30° C. will then result in plasmid vector loss from a population of cells growing at temperatures below 30° C. This will result in a loss of the ability to synthesize Asd, which in turn will reduce, and ultimately eliminate, synthesis of DAP. As described earlier, since DAP is an essential constituent of the rigid layer of the bacterial cell wall, the absence of DAP will cause DAP-less death and lysis of cells attempting to grow at temperatures below 30° C.

The *S. typhimurium* polA gene can be isolated from a library of 5 to 7 kb Sau3A fragments of *S. typhimurium* DNA cloned into a low copy-number of polA-independent vector, such as pSC101. The polA clones can be selected for their ability to rescue a polA-dependent plasmid when the library is electroporated into a temperature-sensitive polA mutant χ1891 and cells are grown at 42° C.

Inverse PCR amplification of the *S. typhimurium* polA gene can then be performed using primers designed to eliminate the promoter region of polA but retain the Shine-Dalgarno sequence for translation initiation. The polA promoter will then be replaced with the bacteriophage lambda promoter left, which is regulated by the temperature-sensitive CI857 repressor.

This temperature regulated polA cartridge can then be transferred to a pir-dependent suicide vector, such as pMEG-011 and electroporated in a *S. typhimurium* host, such as MGN-392. By using *S. typhimurium* strains lacking the pir gene required for replication of the suicide vector, the suicide vector, with the temperature regulated polA gene, will integrate into the chromosome via a single recombinational event. Subsequent selection against the tetracycline resistance element on the suicide vector using fusaric acid will allow isolation of strains that have undergone a second crossover event replacing the wild-type polA gene with the temperature regulated polA gene. The resulting strain will thus provide temperature-regulated expression polA and temperature-regulated expression of C2 (from the cI857PRc2 cartridge inserted in the defined deletion of asd). The ELVS vector pMEG-104, or a derivative with a foreign gene inserted into the multiple cloning site downstream from Ptrc, could then be introduced into the strain. This strain will grow at 37° C. However, at temperatures below 30° C., the strain will undergo DAP-less death due to both the inability to maintain the plasmid vector with the asd gene and the inability to express asd, and the strain will also lyse due to the expression of phage lysis genes lys13 and lys19.

Example 4
Construction of a Chromosomally Based Environmentally Limited Viability System The same components described in the construction of a vector based thermoregulated Environmentally Limited Viability System can be adapted to make a chromosomally based ELVS. The defined asd deletion containing the cI857PRc2 cartridge can first be introduced into a bacterial strain with properties desirable for its intended use, such as use as a vaccine or in a fermentation to produce a high-value product. The integration of the defined asd deletion containing the cI857PRc2 cartridge can be accomplished using the same procedure as described above for the construction of MGN-392. The thermoregulated asd lysis cartridge from pMEG-104 can then be transferred to a suicide vector containing a defined deletion of a selected gene. The chromosomal copy of the selected gene will be the target site of chromosomal integration for the asd lysis cartridge. If the host cell is a pathogen, it is preferred that the selected gene be a gene whose inactivation will attenuate the host cell and render it avirulent and immunogenic, as would be the case for a vaccine strain. Such selected genes could be, for example, cya, crp, phoP, aroA, aroC, aroD, ompR, htrA, and cdt. Alternatively, the selected gene could be a dispensable gene so that the engineered strain would have no noticeable defect. For fermentation strains, the selected gene could be chosen such that its inactivation will result in a fermentation production strain with improved production properties, such as a lessened ability to degrade expressed foreign gene products.

The suicide vector containing the asd lysis cartridge inserted into selected gene with the defined deletion can then be electroporated into a strain with a defined asd deletion containing the cI857PRc2 regulatory cartridge. Integration can be accomplished by selecting for first and second recombinational events as described above. The resulting strain will possess all components of the ELVS on the chromosome. If this strain were to be used as a vaccine, the expression of foreign antigens could be achieved by integrating the expression system for that foreign antigen into the chromosome. Alternatively, the gene for the foreign antigen could be contained on a plasmid vector lacking a drug resistance gene but containing a wild-type gene, such as purA or carA. Such a vector-borne gene would be essential for growth and replication inside an animal host of a vaccine strain with a ΔpurA or ΔcarA chromosomal mutation. Similar considerations could be used to establish a vector system for a fermentation production strain with a chromosomally located ELVS in order to achieve high-level expression of a foreign gene product.

Example 5
Construction and in vitro Testing of an Arabinose Regulated Environmentally Limited Viability System This example describes the construction of the arabinose regulated ELVS and in vitro demonstration of its effectiveness. The methods used to produce the components of the arabinose regulated ELVS illustrated in FIG. 13 employed standard molecular cloning techniques. The ELVS depicted in FIG. 13 is an arabinose regulated delayed death Environmentally Limited Viability System with a chromosomally encoded C2 repressor. The presence of arabinose results in the production of the C2 repressor which in turn prevents the expression of the lysis genes, as shown on the two alternative plasmids pMEG-104 and pMEG-209. The construction of the ELVS plasmid, pMEG-104, is described in Example 1. The alternative ELVS plasmid pMEG-209 was constructed from pMEG-104 by deleting the $\lambda P_L$ with the restriction enzymes BglII and NdeI and replacing it with the $\lambda CI857P_R$ BamHI to NdeI fragment of pMEG-014, providing both the λcI regulated promoter right and the thermosensitive CI857 repressor at high levels. The chromosomally encoded P22 C2 repressor is provided by the arabinose regulated BAD promoter transcribing the c2 gene inserted into the asd-19 deletion. The chromosomal integration of the asd-19 deletion containing c2 with $P_{BAD}$ regulation was obtained using the suicide plasmid pMEG-221 (Table 2).

In vitro analysis of the effectiveness of the arabinose regulated lysis system was determined using MGN-797 (Table 1) containing the original ELVS plasmid, pMEG-104, and the chromosomal arabinose regulated C2 repressor as shown in FIG. 13. In this example, death of MGN-797 cells in a non-permissive environment (that is, an environment lacking arabinose) is the result of expression of the lysis proteins following dilution of the C2 repressor in growing cells. MGN-797 (with pMEG-104) was grown for 12 to 16 hours without aeration in Lennox broth containing 0.2% arabinose prior to diluting 1/1000 into Lennox broth either with or without 0.2% arabinose. The graph in FIG. 14 shows the growth of the MGN-797 ELVS following transfer of cells to media either lacking or containing 0.2% arabinose. As shown by the dashed line with the circular dots in FIG. 14, MGN-797 cells begin to die only after 2 hours following transfer to the non-permissive environment lacking arabinose. This result demonstrates temporary viability of an ELVS in a non-permissive environment, and supports the expectation that such a containment system can remain viable temporarily within a host animal (long enough to produce an effect) while reducing persistence and shedding, and preventing proliferation and horizontal transfer of the ELVS strain in the environment. Introduction of this arabinose regulated system, or similar regulatory systems as described herein, into an attenuated vaccine strain could then be used to produce a protective immune response in an animal while reducing carriage and shedding by the host animal.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An isolated microbial cell comprising a genetically engineered Environmentally Limited Viability System, wherein the cell is viable in a permissive environment and non-viable or temporarily viable in a non-permissive environment, the system comprising
   (a) an essential gene located on an extrachromosomal vector, wherein expression of the essential gene in the cell is essential to the viability of the cell, the essential gene is expressed when the cell is in the permissive environment and is not expressed or temporarily expressed when the cell is in the non-permissive environment, and wherein the essential gene is a copy of a wild-type gene of the microbial cell; and
   (b) a lethal gene located on an extrachromosomal vector, wherein the expression of the lethal gene is regulated by an expression product of a regulatory gene located on the chromosome of the cell, and wherein expression of the lethal gene is lethal to the cell and the lethal gene is expressed when the cell is in the non-permissive environment but not when the cell is in the permissive environment,
   wherein the wild-type essential gene is inactivated in the cell, and wherein the essential gene is essential for metabolism, growth, cell wall integrity, or cell membrane integrity of the cell.

2. The cell of claim 1 wherein the cell grows in the permissive environment and dies in the non-permissive environment.

3. The cell of claim 1 wherein the permissive environment comprises an environment containing a nutrient required to maintain expression of the essential gene, prevent expression of the lethal gene, or both, and the non-permissive environment comprises an environment lacking the nutrient.

4. The cell of claim 1 wherein the permissive environment is inside a warm-blooded animal and the non-permissive environment is outside a warm-blooded animal.

5. The cell of claim 1, wherein the essential gene comprises the asd gene operatively linked to araC-$P_{BAD}$.

6. The cell of claim 1 wherein the expression product of the regulatory gene inhibits expression of the lethal gene, and wherein the regulatory gene is expressed or active only in the permissive environment.

7. The cell of claim 1 wherein the vector has two lethal genes.

8. The cell of claim 1 wherein the cell is a gram-negative bacterium.

9. The cell of claim 8 wherein the gram-negative bacterium is an enteric bacterium.

10. The cell of claim 9 wherein the genus of the enteric bacterium is selected from the group consisting of Escherichia and Salmonella.

11. The cell of claim 1, wherein expression of the essential gene is regulated by an expression product of a regulatory gene, wherein the expression product of the regulatory gene inhibits expression of the essential gene and is expressed or active only in the non-permissive environment, and wherein the essential gene comprises the asd gene operatively linked to araC-$P_{BAD}$.

12. The cell of claim 1 further comprising an expression gene wherein the expression gene encodes a desired expression product.

13. The cell of claim 1 wherein the cell is temporarily viable in the non-permissive environment.

14. The cell of claim 1 further comprising a transfer vector.

15. The cell of claim 1 wherein the lethal gene is a gene required for excision of a prophage, wherein the prophage is in the chromosome of the cell, and wherein excision of the prophage causes lysis of the cell.

16. The cell of claim 1 wherein the essential gene, the lethal gene, or both have engineered expression.

* * * * *